United States Patent
Stone

(10) Patent No.: US 8,317,825 B2
(45) Date of Patent: Nov. 27, 2012

(54) SOFT TISSUE CONDUIT DEVICE AND METHOD

(75) Inventor: Kevin T. Stone, Winona Lake, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 678 days.

(21) Appl. No.: 12/419,491

(22) Filed: Apr. 7, 2009

(65) Prior Publication Data

US 2009/0192468 A1 Jul. 30, 2009

Related U.S. Application Data

(60) Division of application No. 11/408,282, filed on Apr. 20, 2006, now abandoned, which is a continuation-in-part of application No. 11/347,661, filed on Feb. 3, 2006, now Pat. No. 7,749,250, and a continuation-in-part of application No. 11/294,694, filed on Dec. 5, 2005, now Pat. No. 7,914,539, which is a continuation-in-part of application No. 10/984,624, filed on Nov. 9, 2004, now Pat. No. 7,608,098.

(51) Int. Cl.
*A61B 17/58* (2006.01)

(52) U.S. Cl. ............ 606/213; 604/93.01; 604/500; 424/422; 606/139; 606/232

(58) Field of Classification Search .......... 606/72, 606/74, 232, 213, 151, 139, 144, 148, 300–301, 606/304; 128/898; 623/1.42–1.48, 1.27, 623/13.13–13.17; 424/422–423; 604/93.01, 604/500
See application file for complete search history.

(56) References Cited

U.S. PATENT DOCUMENTS

| | | |
|---|---|---|
| 26,501 A | 10/1859 | Kendrick et al. |
| 65,499 A | 6/1867 | Miller |
| 126,366 A | 4/1872 | Wills |
| 233,475 A | 10/1880 | Cook et al. |
| 261,501 A | 7/1882 | Vandermark |
| 268,407 A | 12/1882 | Hughes |
| 330,087 A | 11/1885 | Binns |
| 417,805 A | 12/1889 | Beaman |
| 487,304 A | 12/1892 | Todd |
| 762,710 A | 6/1901 | Hall |
| 837,767 A | 12/1906 | Aims |
| 838,203 A | 12/1906 | Neil |

(Continued)

FOREIGN PATENT DOCUMENTS

AU 4957264 3/1966

(Continued)

OTHER PUBLICATIONS

"Do your next distal tendon repair with . . . The Lubbers Technique", Teno Fix® brochure, 2003 (2 pages) Ortheon® Medical.

(Continued)

*Primary Examiner* — Corrine M McDermott
*Assistant Examiner* — Mark Mashack
(74) *Attorney, Agent, or Firm* — Harness, Dickey

(57) ABSTRACT

A method of conducting biological materials in soft tissue includes inserting an elongated conduit device into the soft tissue and through a defect in the soft tissue, and conducting biological materials along at least one longitudinal channel defined on an outer surface of the conduit device into the soft tissue. The conduit device is externally threaded.

14 Claims, 8 Drawing Sheets

U.S. PATENT DOCUMENTS

| | | |
|---|---|---|
| 1,059,631 A | 4/1913 | Popovics |
| 1,131,155 A | 3/1915 | Murphy |
| 1,153,450 A | 9/1915 | Schaff |
| 1,346,940 A | 7/1920 | Collins |
| 1,635,066 A | 7/1927 | Wells |
| 401,677 A | 11/1933 | Autenrieth |
| 1,950,799 A | 3/1934 | Jones |
| 2,065,659 A | 12/1936 | Cullen |
| 2,108,206 A | 2/1938 | Meeker |
| 2,121,193 A | 6/1938 | Hanicke |
| 2,242,003 A | 5/1941 | Lorenzo |
| 2,267,925 A | 12/1941 | Johnston |
| 2,302,986 A | 11/1942 | Vollrath |
| 2,329,398 A | 9/1943 | Duffy |
| 2,397,216 A | 3/1946 | Stellin |
| RE22,857 E | 3/1947 | Ogburn |
| 2,526,959 A | 10/1950 | Lorenzo |
| 2,528,456 A | 10/1950 | Stevenson |
| 2,562,419 A | 7/1951 | Ferris |
| 2,581,564 A | 1/1952 | Villegas |
| 2,600,395 A | 6/1952 | Domoj et al. |
| 2,610,631 A | 9/1952 | Calicchio |
| 2,665,597 A | 1/1954 | Hill |
| 2,669,774 A | 2/1954 | Mitchell |
| 2,698,986 A | 1/1955 | Brown |
| 2,760,488 A | 8/1956 | Pierce |
| 2,833,284 A | 5/1958 | Springer |
| 2,846,712 A | 8/1958 | Markman |
| 2,860,393 A | 11/1958 | Brock |
| 2,880,728 A | 4/1959 | Rights |
| 2,881,762 A | 4/1959 | Lowrie |
| 2,883,096 A | 4/1959 | Dawson |
| 2,913,042 A | 11/1959 | Taylor |
| 3,000,009 A | 9/1961 | Selstad |
| 3,003,155 A | 10/1961 | Mielzynski et al. |
| 3,013,559 A | 12/1961 | Thomas |
| 3,037,619 A | 6/1962 | Stevans |
| 3,039,460 A | 6/1962 | Chandler |
| 3,090,386 A | 5/1963 | Curtis |
| 3,103,666 A | 9/1963 | Bone |
| 3,123,077 A | 3/1964 | Alcamo |
| 3,125,095 A | 3/1964 | Kaufman et al. |
| 3,209,422 A | 10/1965 | Dritz |
| 3,234,938 A | 2/1966 | Robinson |
| 3,240,379 A | 3/1966 | Bremer et al. |
| 3,250,271 A | 5/1966 | Lippes |
| 3,399,432 A | 9/1968 | Merser |
| 3,409,014 A | 11/1968 | Shannon |
| 3,435,475 A | 4/1969 | Bisk |
| 3,467,089 A | 9/1969 | Hasson |
| 3,470,834 A | 10/1969 | Bone |
| 3,470,875 A | 10/1969 | Johnson |
| 3,500,820 A | 3/1970 | Almen |
| 3,507,274 A | 4/1970 | Soichet |
| 3,513,484 A | 5/1970 | Hausner |
| 3,515,132 A | 6/1970 | McKnight |
| 3,522,803 A | 8/1970 | Majzlin |
| 3,527,223 A | 9/1970 | Shein |
| 3,533,406 A | 10/1970 | Hutterer et al. |
| 3,541,591 A | 11/1970 | Hoegerman |
| 3,547,389 A | 12/1970 | Mitchell |
| 3,579,831 A | 5/1971 | Stevens et al. |
| 3,590,616 A | 7/1971 | Schussler et al. |
| 3,608,095 A | 9/1971 | Barry |
| 3,618,447 A | 11/1971 | Goins |
| 3,628,530 A | 12/1971 | Schwartz |
| 3,643,649 A | 2/1972 | Amato |
| 3,648,705 A | 3/1972 | Lary |
| 3,656,483 A | 4/1972 | Rudel |
| 3,659,597 A | 5/1972 | Wolfers |
| 3,664,345 A | 5/1972 | Dabbs et al. |
| 3,665,560 A | 5/1972 | Bennett et al. |
| 3,675,639 A | 7/1972 | Cimber |
| 3,683,422 A | 8/1972 | Stemmer et al. |
| 3,692,022 A | 9/1972 | Ewing |
| 3,695,271 A | 10/1972 | Chodorow |
| 3,699,969 A | 10/1972 | Allen |
| 3,716,058 A | 2/1973 | Tanner, Jr. |
| 3,744,488 A | 7/1973 | Cox |
| 3,752,516 A | 8/1973 | Mumma |
| 3,757,629 A | 9/1973 | Schneider |
| 3,763,856 A | 10/1973 | Blomberg |
| 3,771,520 A | 11/1973 | Lerner |
| 3,777,748 A | 12/1973 | Abramson |
| 3,807,407 A | 4/1974 | Schweizer |
| 3,810,456 A | 5/1974 | Karman |
| 3,825,010 A | 7/1974 | McDonald |
| 3,840,017 A | 10/1974 | Violante et al. |
| 3,842,824 A | 10/1974 | Neufeld |
| 3,842,840 A | 10/1974 | Schweizer |
| 3,845,772 A | 11/1974 | Smith |
| 3,867,933 A | 2/1975 | Kitrilakis |
| 3,867,944 A | 2/1975 | Samuels |
| 3,871,368 A | 3/1975 | Johnson et al. |
| 3,871,379 A | 3/1975 | Clarke |
| 3,874,388 A | 4/1975 | King et al. |
| 3,875,648 A | 4/1975 | Bone |
| 3,877,570 A | 4/1975 | Barry |
| 3,880,156 A | 4/1975 | Hoff |
| 3,881,475 A | 5/1975 | Gordon et al. |
| 3,889,666 A | 6/1975 | Lerner |
| 3,892,240 A | 7/1975 | Park |
| 3,896,500 A | 7/1975 | Rambert et al. |
| 3,907,442 A | 9/1975 | Reid |
| 3,910,281 A | 10/1975 | Kletschka et al. |
| 3,918,444 A | 11/1975 | Hoff et al. |
| 3,918,455 A | 11/1975 | Coplan |
| 3,927,666 A | 12/1975 | Hoff |
| 3,931,667 A | 1/1976 | Merser et al. |
| 3,933,153 A | 1/1976 | Csatary et al. |
| 3,937,217 A | 2/1976 | Kosonen et al. |
| 3,943,932 A | 3/1976 | Woo |
| 3,946,728 A | 3/1976 | Bettex et al. |
| 3,946,740 A | 3/1976 | Bassett |
| 3,953,896 A | 5/1976 | Treace |
| 3,954,103 A | 5/1976 | Garcia-Roel et al. |
| 3,961,632 A | 6/1976 | Moossun |
| 3,973,560 A | 8/1976 | Emmett et al. |
| 3,976,079 A | 8/1976 | Samuels et al. |
| 3,977,050 A | 8/1976 | Perez et al. |
| 3,979,799 A | 9/1976 | Merser et al. |
| 3,985,138 A | 10/1976 | Jarvik |
| 3,990,619 A | 11/1976 | Russell |
| 4,005,707 A | 2/1977 | Moulding, Jr. |
| 4,006,747 A | 2/1977 | Kronenthal et al. |
| 4,007,743 A | 2/1977 | Blake |
| 4,013,071 A | 3/1977 | Rosenberg et al. |
| 4,026,281 A | 5/1977 | Mayberry et al. |
| 4,036,101 A | 7/1977 | Burnett |
| 4,050,100 A | 9/1977 | Barry |
| 4,054,954 A | 10/1977 | Nakayama et al. |
| 4,084,478 A | 4/1978 | Simmons |
| 4,085,466 A | 4/1978 | Goodfellow et al. |
| 4,094,313 A | 6/1978 | Komamura et al. |
| 4,099,750 A | 7/1978 | McGrew |
| 4,103,690 A | 8/1978 | Harris |
| RE29,819 E | 10/1978 | Bone |
| 4,121,487 A | 10/1978 | Bone |
| 4,143,656 A | 3/1979 | Holmes et al. |
| 4,144,876 A | 3/1979 | DeLeo |
| 4,149,277 A | 4/1979 | Bokros |
| 4,157,714 A | 6/1979 | Foltz et al. |
| 4,160,453 A | 7/1979 | Miller |
| 4,164,225 A | 8/1979 | Johnson et al. |
| 4,172,458 A | 10/1979 | Pereyra |
| 4,175,555 A | 11/1979 | Herbert et al. |
| 4,185,636 A | 1/1980 | Gabbay et al. |
| 4,196,883 A | 4/1980 | Einhorn et al. |
| 4,210,148 A | 7/1980 | Stivala |
| 4,235,161 A | 11/1980 | Kunreuther |
| 4,235,238 A | 11/1980 | Ogiu et al. |
| 4,237,779 A | 12/1980 | Kunreuther |
| 4,243,037 A | 1/1981 | Smith |
| 4,249,525 A | 2/1981 | Krzeminski |
| 4,263,913 A | 4/1981 | Malmin |
| 4,265,246 A | 5/1981 | Barry |
| 4,273,117 A | 6/1981 | Neuhauser et al. |

| | | | | | |
|---|---|---|---|---|---|
| 4,275,717 A | 6/1981 | Bolesky | 4,760,843 A | 8/1988 | Fischer et al. |
| 4,287,807 A | 9/1981 | Pacharis et al. | 4,760,844 A | 8/1988 | Kyle |
| 4,291,698 A | 9/1981 | Fuchs et al. | 4,760,848 A | 8/1988 | Hasson |
| 4,301,551 A | 11/1981 | Dore et al. | 4,770,663 A | 9/1988 | Hanslik et al. |
| 4,307,723 A * | 12/1981 | Finney .............................. 604/8 | 4,772,261 A | 9/1988 | Von Hoff et al. |
| 4,312,337 A | 1/1982 | Donohue | 4,772,286 A | 9/1988 | Goble et al. |
| 4,316,469 A | 2/1982 | Kapitanov et al. | 4,773,910 A | 9/1988 | Chen et al. |
| 4,326,531 A | 4/1982 | Shimonaka et al. | 4,775,380 A | 10/1988 | Seedhom et al. |
| 4,345,601 A | 8/1982 | Fukuda | 4,776,328 A | 10/1988 | Frey et al. |
| 4,349,027 A | 9/1982 | DiFrancesco | 4,781,190 A | 11/1988 | Lee et al. |
| 4,388,921 A | 6/1983 | Sutter et al. | 4,784,126 A | 11/1988 | Hourahane et al. |
| 4,400,833 A | 8/1983 | Kurland | 4,787,882 A | 11/1988 | Claren et al. |
| 4,402,445 A | 9/1983 | Green | 4,790,297 A | 12/1988 | Luque et al. |
| 4,409,974 A | 10/1983 | Freedland | 4,793,363 A | 12/1988 | Ausherman et al. |
| 4,438,769 A | 3/1984 | Pratt et al. | 4,809,695 A | 3/1989 | Gwathmey et al. |
| 4,441,489 A | 4/1984 | Evans et al. | 4,813,406 A | 3/1989 | Ogle, II |
| 4,454,875 A | 6/1984 | Pratt et al. | 4,823,794 A | 4/1989 | Pierce |
| 4,462,395 A | 7/1984 | Johnson | 4,828,562 A | 5/1989 | Kenna |
| 4,463,753 A | 8/1984 | Gustilo | 4,832,026 A | 5/1989 | Jones |
| 4,473,102 A | 9/1984 | Ohman et al. | 4,834,098 A | 5/1989 | Jones |
| 4,484,570 A | 11/1984 | Sutter et al. | 4,838,282 A | 6/1989 | Strasser et al. |
| 4,489,446 A | 12/1984 | Reed | 4,841,960 A | 6/1989 | Garner |
| 4,493,323 A | 1/1985 | Albright et al. | 4,851,005 A | 7/1989 | Hunt et al. |
| 4,496,468 A | 1/1985 | House et al. | 4,858,608 A | 8/1989 | McQuilkin et al. |
| 4,505,274 A | 3/1985 | Speelman | 4,860,513 A | 8/1989 | Whitman |
| 4,509,516 A | 4/1985 | Richmond | 4,863,383 A | 9/1989 | Grafelmann et al. |
| 4,531,522 A | 7/1985 | Bedi et al. | 4,870,957 A | 10/1989 | Goble et al. |
| 4,532,926 A | 8/1985 | O'Holla | 4,873,976 A | 10/1989 | Schreiber |
| 4,534,350 A | 8/1985 | Golden et al. | 4,887,601 A | 12/1989 | Richards |
| 4,535,764 A | 8/1985 | Ebert | 4,890,615 A | 1/1990 | Caspari et al. |
| 4,537,185 A | 8/1985 | Stednitz | 4,893,619 A | 1/1990 | Dale et al. |
| 4,549,545 A | 10/1985 | Levy | 4,893,974 A | 1/1990 | Fischer et al. |
| 4,549,652 A | 10/1985 | Free | 4,895,148 A | 1/1990 | Bays et al. |
| 4,561,432 A | 12/1985 | Mazor | 4,896,668 A | 1/1990 | Popoff et al. |
| 4,564,007 A | 1/1986 | Coombs et al. | 4,898,156 A | 2/1990 | Gatturna et al. |
| 4,570,623 A | 2/1986 | Ellison et al. | 4,899,743 A | 2/1990 | Nicholson et al. |
| 4,573,844 A | 3/1986 | Smith | 4,901,721 A | 2/1990 | Hakki |
| 4,576,608 A | 3/1986 | Homsy | 4,923,461 A | 5/1990 | Caspari et al. |
| 4,584,722 A | 4/1986 | Levy et al. | 4,927,421 A | 5/1990 | Goble et al. |
| 4,590,928 A | 5/1986 | Hunt et al. | 4,946,468 A | 8/1990 | Li |
| 4,595,007 A | 6/1986 | Mericle | 4,950,270 A | 8/1990 | Bowman et al. |
| 4,596,249 A | 6/1986 | Freda et al. | 4,950,285 A | 8/1990 | Wilk |
| 4,602,635 A | 7/1986 | Mulhollan et al. | 4,960,381 A | 10/1990 | Niznick |
| 4,602,636 A | 7/1986 | Noiles | 4,961,741 A | 10/1990 | Hayhurst |
| 4,604,997 A | 8/1986 | De Bastiani et al. | 4,968,315 A | 11/1990 | Gatturna |
| 4,605,414 A | 8/1986 | Czajka | 4,968,317 A | 11/1990 | Tormala et al. |
| 4,616,650 A | 10/1986 | Green et al. | 4,969,886 A | 11/1990 | Cziffer et al. |
| 4,621,640 A | 11/1986 | Mulhollan et al. | 4,974,488 A | 12/1990 | Spralja |
| 4,624,254 A | 11/1986 | McGarry et al. | 4,976,736 A | 12/1990 | White et al. |
| 4,632,100 A | 12/1986 | Somers et al. | 4,978,350 A | 12/1990 | Wagenknecht et al. |
| 4,635,637 A | 1/1987 | Schreiber | 4,979,956 A | 12/1990 | Silvestrini |
| 4,636,121 A | 1/1987 | Miller | 4,983,176 A | 1/1991 | Cushman et al. |
| 4,641,652 A | 2/1987 | Hutterer et al. | 4,988,351 A | 1/1991 | Paulos et al. |
| 4,649,952 A | 3/1987 | Jobe | 4,994,074 A | 2/1991 | Bezwada et al. |
| 4,653,486 A | 3/1987 | Coker | 4,997,433 A | 3/1991 | Goble et al. |
| 4,653,487 A | 3/1987 | Maale | 5,002,550 A | 3/1991 | Li |
| 4,653,489 A | 3/1987 | Tronzo | 5,002,562 A | 3/1991 | Oberlander |
| 4,655,777 A | 4/1987 | Dunn et al. | 5,007,921 A | 4/1991 | Brown |
| 4,662,068 A | 5/1987 | Polonsky | 5,030,224 A | 7/1991 | Wright et al. |
| 4,667,662 A | 5/1987 | Titone et al. | 5,037,422 A | 8/1991 | Hayhurst et al. |
| 4,667,675 A | 5/1987 | Davis | 5,041,129 A | 8/1991 | Hayhurst et al. |
| 4,669,473 A | 6/1987 | Richards et al. | 5,046,513 A | 9/1991 | Gatturna et al. |
| 4,683,895 A | 8/1987 | Pohndorf | 5,047,030 A | 9/1991 | Draenert et al. |
| 4,688,561 A | 8/1987 | Reese | 5,053,046 A | 10/1991 | Janese |
| 4,690,169 A | 9/1987 | Jobe | 5,053,047 A | 10/1991 | Yoon |
| 4,705,040 A | 11/1987 | Mueller et al. | 5,059,201 A | 10/1991 | Asnis |
| 4,708,132 A | 11/1987 | Silvestrini | 5,059,206 A | 10/1991 | Winters |
| 4,716,893 A | 1/1988 | Fischer et al. | 5,061,277 A | 10/1991 | Carpentier et al. |
| 4,719,671 A | 1/1988 | Ito et al. | 5,062,344 A | 11/1991 | Gerker |
| 4,719,917 A | 1/1988 | Barrows et al. | 5,062,843 A | 11/1991 | Mahony, III |
| 4,723,540 A | 2/1988 | Gilmer, Jr. | 5,064,431 A | 11/1991 | Gilbertson et al. |
| 4,724,839 A | 2/1988 | Bedi et al. | 5,074,874 A | 12/1991 | Yoon et al. |
| 4,728,332 A | 3/1988 | Albrektsson et al. | 5,078,731 A | 1/1992 | Hayhurst |
| 4,738,255 A | 4/1988 | Goble et al. | 5,078,843 A | 1/1992 | Pratt |
| 4,741,330 A | 5/1988 | Hayhurst | 5,084,050 A | 1/1992 | Draenert et al. |
| 4,741,336 A | 5/1988 | Failla et al. | 5,084,058 A | 1/1992 | Li |
| 4,744,353 A | 5/1988 | McFarland | 5,085,661 A | 2/1992 | Moss |
| 4,744,793 A | 5/1988 | Parr et al. | 5,087,263 A | 2/1992 | Li |
| 4,750,492 A | 6/1988 | Jacobs | 5,087,309 A | 2/1992 | Melton, Jr. |

| | | | | | | |
|---|---|---|---|---|---|---|
| 5,092,866 A | 3/1992 | Breard et al. | | 5,354,298 A | 10/1994 | Lee et al. |
| 5,098,435 A | 3/1992 | Stednitz et al. | | 5,356,413 A | 10/1994 | Martins et al. |
| 5,100,415 A | 3/1992 | Hayhurst | | 5,358,511 A | 10/1994 | Gatturna et al. |
| 5,100,417 A | 3/1992 | Cerier et al. | | 5,360,431 A | 11/1994 | Puno et al. |
| 5,116,337 A | 5/1992 | Johnson | | 5,362,294 A | 11/1994 | Seitzinger |
| 5,116,373 A | 5/1992 | Jakob et al. | | 5,364,400 A | 11/1994 | Rego, Jr. et al. |
| 5,116,375 A | 5/1992 | Hofmann | | 5,368,599 A | 11/1994 | Hirsch et al. |
| 5,123,913 A | 6/1992 | Wilk et al. | | 5,370,661 A | 12/1994 | Branch |
| 5,123,914 A | 6/1992 | Cope | | 5,370,662 A | 12/1994 | Stone et al. |
| 5,127,785 A | 7/1992 | Faucher et al. | | 5,372,146 A | 12/1994 | Branch |
| 5,129,901 A | 7/1992 | Decoste | | 5,372,604 A | 12/1994 | Trott |
| 5,129,902 A | 7/1992 | Goble et al. | | 5,372,821 A | 12/1994 | Badylak et al. |
| 5,129,904 A | 7/1992 | Illi et al. | | 5,374,268 A | 12/1994 | Sander |
| 5,129,906 A | 7/1992 | Ross et al. | | 5,379,492 A | 1/1995 | Glesser |
| 5,139,499 A | 8/1992 | Small et al. | | 5,383,878 A | 1/1995 | Roger et al. |
| 5,139,520 A | 8/1992 | Rosenberg | | 5,383,904 A | 1/1995 | Totakura et al. |
| 5,143,498 A | 9/1992 | Whitman | | 5,391,171 A | 2/1995 | Schmieding |
| 5,147,362 A | 9/1992 | Goble | | 5,391,176 A | 2/1995 | de la Torre |
| 5,149,329 A | 9/1992 | Richardson | | 5,393,302 A | 2/1995 | Clark et al. |
| 5,152,790 A | 10/1992 | Rosenberg et al. | | RE34,871 E | 3/1995 | McGuire et al. |
| 5,154,189 A | 10/1992 | Oberlander | | 5,397,356 A | 3/1995 | Goble et al. |
| 5,156,616 A | 10/1992 | Meadows et al. | | 5,403,328 A | 4/1995 | Shallman |
| 5,163,960 A | 11/1992 | Bonutti | | 5,403,329 A | 4/1995 | Hinchcliffe |
| D331,626 S | 12/1992 | Hayhurst et al. | | 5,403,348 A | 4/1995 | Bonutti |
| 5,169,400 A | 12/1992 | Muhling et al. | | 5,417,691 A | 5/1995 | Hayhurst |
| 5,176,682 A | 1/1993 | Chow | | 5,417,712 A | 5/1995 | Whittaker et al. |
| 5,178,629 A | 1/1993 | Kammerer | | 5,423,819 A | 6/1995 | Small et al. |
| 5,183,458 A | 2/1993 | Marx | | 5,423,823 A | 6/1995 | Schmieding |
| 5,192,282 A | 3/1993 | Draenert et al. | | 5,423,860 A | 6/1995 | Lizardi et al. |
| 5,197,987 A | 3/1993 | Koch et al. | | 5,425,733 A | 6/1995 | Schmieding |
| 5,203,784 A | 4/1993 | Ross et al. | | 5,425,766 A | 6/1995 | Bowald et al. |
| 5,203,787 A | 4/1993 | Noblitt et al. | | 5,433,751 A | 7/1995 | Christel et al. |
| 5,207,679 A | 5/1993 | Li | | 5,437,680 A | 8/1995 | Yoon |
| 5,209,753 A | 5/1993 | Biedermann et al. | | 5,439,684 A | 8/1995 | Prewett et al. |
| 5,209,805 A | 5/1993 | Spraggins | | 5,441,508 A | 8/1995 | Gazielly et al. |
| 5,211,647 A | 5/1993 | Schmieding | | 5,443,468 A | 8/1995 | Johnson |
| 5,211,650 A | 5/1993 | Noda | | 5,443,482 A | 8/1995 | Stone et al. |
| 5,214,987 A | 6/1993 | Fenton, Sr. | | 5,443,483 A | 8/1995 | Kirsch et al. |
| 5,219,359 A | 6/1993 | McQuilkin et al. | | 5,443,509 A | 8/1995 | Boucher et al. |
| 5,222,976 A | 6/1993 | Yoon | | 5,445,833 A | 8/1995 | Badylak et al. |
| 5,224,946 A | 7/1993 | Hayhurst et al. | | 5,447,512 A | 9/1995 | Wilson et al. |
| 5,230,699 A | 7/1993 | Grasinger | | 5,451,203 A | 9/1995 | Lamb |
| 5,232,436 A | 8/1993 | Janevski | | 5,454,811 A | 10/1995 | Huebner |
| 5,234,435 A | 8/1993 | Seagrave, Jr. | | 5,456,685 A | 10/1995 | Huebner |
| 5,235,238 A | 8/1993 | Nomura et al. | | 5,456,722 A | 10/1995 | McLeod et al. |
| 5,236,445 A | 8/1993 | Hayhurst et al. | | 5,458,601 A | 10/1995 | Young, Jr. et al. |
| 5,236,461 A | 8/1993 | Forte | | 5,458,604 A | 10/1995 | Schmieding |
| 5,242,447 A | 9/1993 | Borzone | | 5,462,560 A | 10/1995 | Stevens |
| 5,246,441 A | 9/1993 | Ross et al. | | 5,464,426 A | 11/1995 | Bonutti |
| 5,249,899 A | 10/1993 | Wilson | | 5,464,427 A | 11/1995 | Curtis et al. |
| 5,258,015 A | 11/1993 | Li et al. | | 5,464,440 A | 11/1995 | Johansson et al. |
| 5,258,016 A | 11/1993 | DiPoto et al. | | 5,466,237 A | 11/1995 | Byrd, III et al. |
| 5,258,040 A | 11/1993 | Bruchman et al. | | 5,467,786 A | 11/1995 | Allen et al. |
| 5,268,001 A | 12/1993 | Nicholson et al. | | 5,470,334 A | 11/1995 | Ross et al. |
| 5,269,160 A | 12/1993 | Wood | | 5,470,337 A | 11/1995 | Moss |
| 5,269,783 A | 12/1993 | Sander | | 5,470,338 A | 11/1995 | Whitfield et al. |
| 5,269,809 A | 12/1993 | Hayhurst et al. | | 5,472,452 A | 12/1995 | Trott |
| 5,281,422 A | 1/1994 | Badylak et al. | | 5,474,565 A | 12/1995 | Trott |
| 5,282,809 A | 2/1994 | Kammerer et al. | | 5,474,568 A | 12/1995 | Scott |
| 5,282,832 A | 2/1994 | Toso et al. | | 5,474,572 A | 12/1995 | Hayhurst |
| 5,282,867 A | 2/1994 | Mikhail | | 5,478,344 A | 12/1995 | Stone et al. |
| 5,285,040 A | 2/1994 | Brandberg et al. | | 5,478,345 A | 12/1995 | Stone et al. |
| 5,290,217 A | 3/1994 | Campos | | 5,480,403 A | 1/1996 | Lee et al. |
| 5,306,301 A | 4/1994 | Graf et al. | | 5,480,406 A | 1/1996 | Nolan et al. |
| 5,312,422 A | 5/1994 | Trott | | 5,484,442 A | 1/1996 | Melker et al. |
| 5,312,438 A | 5/1994 | Johnson | | 5,486,197 A | 1/1996 | Le et al. |
| 5,318,577 A | 6/1994 | Li | | 5,490,750 A | 2/1996 | Gundy |
| 5,318,578 A | 6/1994 | Hasson | | 5,496,331 A | 3/1996 | Xu et al. |
| 5,320,115 A | 6/1994 | Kenna | | 5,496,348 A | 3/1996 | Bonutti |
| 5,320,626 A | 6/1994 | Schmieding | | 5,500,000 A | 3/1996 | Feagin et al. |
| 5,320,633 A | 6/1994 | Allen et al. | | 5,505,736 A | 4/1996 | Reimels et al. |
| 5,324,308 A | 6/1994 | Pierce | | 5,507,754 A | 4/1996 | Green et al. |
| 5,334,204 A | 8/1994 | Clewett et al. | | 5,520,691 A | 5/1996 | Branch |
| 5,336,229 A | 8/1994 | Noda | | 5,520,702 A | 5/1996 | Sauer et al. |
| 5,336,231 A | 8/1994 | Adair | | 5,522,817 A | 6/1996 | Sander et al. |
| 5,336,240 A | 8/1994 | Metzler et al. | | 5,522,820 A | 6/1996 | Caspari et al. |
| 5,342,369 A | 8/1994 | Harryman, II | | 5,522,844 A | 6/1996 | Johnson |
| 5,346,462 A | 9/1994 | Barber | | 5,522,845 A | 6/1996 | Wenstrom, Jr. |
| 5,354,292 A | 10/1994 | Braeuer et al. | | 5,522,846 A | 6/1996 | Bonutti |

| | | | | | | |
|---|---|---|---|---|---|---|
| 5,524,946 A | 6/1996 | Thompson | | 5,702,397 A | 12/1997 | Goble et al. |
| 5,527,321 A | 6/1996 | Hinchliffe | | 5,702,422 A | 12/1997 | Stone |
| 5,527,342 A | 6/1996 | Pietrzak et al. | | 5,702,462 A | 12/1997 | Oberlander |
| 5,527,343 A | 6/1996 | Bonutti | | 5,707,373 A | 1/1998 | Sevrain et al. |
| 5,531,759 A | 7/1996 | Kensey et al. | | 5,713,005 A | 1/1998 | Proebsting |
| 5,534,012 A | 7/1996 | Bonutti | | 5,713,904 A | 2/1998 | Errico et al. |
| 5,540,718 A | 7/1996 | Bartlett | | 5,713,905 A | 2/1998 | Goble et al. |
| 5,545,178 A | 8/1996 | Kensey et al. | | 5,713,921 A | 2/1998 | Bonutti |
| 5,545,228 A | 8/1996 | Kambin | | 5,716,359 A | 2/1998 | Ojima et al. |
| 5,549,613 A | 8/1996 | Goble et al. | | 5,716,397 A | 2/1998 | Myers |
| 5,549,617 A | 8/1996 | Green et al. | | 5,718,717 A | 2/1998 | Bonutti |
| 5,549,630 A | 8/1996 | Bonutti | | 5,720,747 A | 2/1998 | Burke |
| 5,549,631 A | 8/1996 | Bonutti | | 5,720,765 A | 2/1998 | Thal |
| 5,562,683 A | 10/1996 | Chan | | 5,720,766 A | 2/1998 | Zang et al. |
| 5,562,685 A | 10/1996 | Mollenauer et al. | | 5,725,549 A | 3/1998 | Lam |
| 5,562,686 A | 10/1996 | Sauer et al. | | 5,725,556 A | 3/1998 | Moser et al. |
| 5,569,269 A | 10/1996 | Hart et al. | | 5,725,581 A | 3/1998 | Brånemark |
| 5,569,305 A | 10/1996 | Bonutti | | 5,725,582 A | 3/1998 | Bevan et al. |
| 5,571,090 A | 11/1996 | Sherts | | 5,726,722 A | 3/1998 | Uehara et al. |
| 5,571,139 A | 11/1996 | Jenkins, Jr. | | 5,728,107 A | 3/1998 | Zlock et al. |
| 5,572,655 A | 11/1996 | Tuljapurkar et al. | | 5,728,109 A | 3/1998 | Schulze et al. |
| 5,573,286 A | 11/1996 | Rogozinski | | 5,728,136 A | 3/1998 | Thal |
| 5,573,542 A | 11/1996 | Stevens | | 5,733,293 A | 3/1998 | Scirica et al. |
| 5,573,548 A | 11/1996 | Nazre et al. | | 5,733,306 A | 3/1998 | Bonutti |
| 5,577,299 A | 11/1996 | Thompson et al. | | 5,733,307 A | 3/1998 | Dinsdale |
| 5,578,057 A | 11/1996 | Wenstrom, Jr. | | 5,735,875 A | 4/1998 | Bonutti et al. |
| 5,584,695 A | 12/1996 | Lal Sachdeva et al. | | 5,741,259 A | 4/1998 | Chan |
| 5,584,835 A | 12/1996 | Greenfield | | 5,741,281 A | 4/1998 | Martin et al. |
| 5,584,836 A | 12/1996 | Ballintyn et al. | | 5,743,912 A | 4/1998 | Lahille et al. |
| 5,584,862 A | 12/1996 | Bonutti | | 5,746,751 A | 5/1998 | Sherts |
| 5,586,986 A | 12/1996 | Hinchliffe | | 5,746,752 A | 5/1998 | Burkhart |
| 5,588,575 A | 12/1996 | Davignon | | 5,746,754 A | 5/1998 | Chan |
| 5,591,180 A | 1/1997 | Hinchliffe | | 5,749,898 A | 5/1998 | Schulze et al. |
| 5,591,181 A | 1/1997 | Stone et al. | | 5,755,729 A | 5/1998 | de la Torre et al. |
| 5,591,207 A | 1/1997 | Coleman | | 5,766,176 A | 6/1998 | Duncan |
| 5,593,407 A | 1/1997 | Reis et al. | | 5,766,250 A | 6/1998 | Chervitz et al. |
| 5,593,425 A | 1/1997 | Bonutti et al. | | 5,769,894 A | 6/1998 | Ferragamo |
| 5,601,557 A | 2/1997 | Hayhurst | | 5,769,899 A | 6/1998 | Schwartz et al. |
| 5,601,559 A | 2/1997 | Melker et al. | | 5,772,673 A | 6/1998 | Cuny et al. |
| 5,601,571 A | 2/1997 | Moss | | 5,776,196 A | 7/1998 | Matsuzaki et al. |
| 5,603,716 A | 2/1997 | Morgan et al. | | 5,782,862 A | 7/1998 | Bonutti |
| 5,607,429 A | 3/1997 | Hayano et al. | | 5,782,864 A | 7/1998 | Lizardi |
| 5,618,290 A | 4/1997 | Toy et al. | | 5,782,866 A | 7/1998 | Wenstrom, Jr. |
| 5,628,756 A | 5/1997 | Barker, Jr. et al. | | 5,785,714 A | 7/1998 | Morgan et al. |
| 5,628,766 A | 5/1997 | Johnson | | 5,792,142 A | 8/1998 | Galitzer |
| 5,630,824 A | 5/1997 | Hart | | 5,792,149 A | 8/1998 | Sherts et al. |
| 5,632,748 A | 5/1997 | Beck, Jr. et al. | | 5,796,127 A | 8/1998 | Hayafuji et al. |
| 5,641,256 A | 6/1997 | Gundy | | 5,797,928 A | 8/1998 | Kogasaka et al. |
| 5,643,266 A | 7/1997 | Li | | 5,800,407 A | 9/1998 | Eldor et al. |
| 5,643,269 A | 7/1997 | Harle et al. | | 5,810,824 A | 9/1998 | Chan |
| 5,643,295 A | 7/1997 | Yoon | | 5,810,848 A | 9/1998 | Hayhurst |
| 5,643,320 A | 7/1997 | Lower et al. | | 5,814,056 A | 9/1998 | Prosst et al. |
| 5,643,321 A | 7/1997 | McDevitt | | 5,814,069 A | 9/1998 | Schulze et al. |
| 5,645,546 A | 7/1997 | Fard | | 5,814,070 A | 9/1998 | Borzone et al. |
| 5,645,547 A | 7/1997 | Coleman | | 5,814,072 A | 9/1998 | Bonutti |
| 5,645,568 A | 7/1997 | Chervitz et al. | | 5,814,073 A | 9/1998 | Bonutti |
| 5,645,588 A | 7/1997 | Graf et al. | | 5,823,980 A | 10/1998 | Kopfer |
| 5,647,874 A | 7/1997 | Hayhurst | | 5,824,011 A | 10/1998 | Stone et al. |
| 5,649,959 A * | 7/1997 | Hannam et al. ............... 606/213 | | 5,824,066 A | 10/1998 | Gross |
| 5,649,963 A | 7/1997 | McDevitt | | 5,843,084 A | 12/1998 | Hart et al. |
| 5,658,289 A | 8/1997 | Boucher et al. | | 5,845,645 A | 12/1998 | Bonutti |
| 5,658,299 A | 8/1997 | Hart | | 5,846,254 A | 12/1998 | Schulze et al. |
| 5,658,313 A | 8/1997 | Thal | | 5,848,983 A | 12/1998 | Basaj et al. |
| 5,662,658 A | 9/1997 | Wenstrom, Jr. | | 5,860,973 A | 1/1999 | Michelson |
| 5,662,663 A | 9/1997 | Shallman | | 5,860,978 A | 1/1999 | McDevitt et al. |
| 5,665,112 A | 9/1997 | Thal | | 5,868,740 A | 2/1999 | LeVeen et al. |
| 5,667,513 A | 9/1997 | Torrie et al. | | 5,868,789 A | 2/1999 | Huebner |
| 5,671,695 A | 9/1997 | Schroeder | | 5,871,484 A | 2/1999 | Spievack et al. |
| 5,674,224 A | 10/1997 | Howell et al. | | 5,871,486 A | 2/1999 | Huebner et al. |
| 5,679,723 A | 10/1997 | Cooper et al. | | 5,871,490 A | 2/1999 | Schulze et al. |
| 5,681,334 A | 10/1997 | Evans et al. | | 5,885,294 A | 3/1999 | Pedlick et al. |
| 5,681,352 A | 10/1997 | Clancy, III et al. | | 5,891,168 A | 4/1999 | Thal |
| 5,683,419 A | 11/1997 | Thal | | 5,893,592 A | 4/1999 | Schulze et al. |
| 5,688,285 A | 11/1997 | Yamada et al. | | 5,895,395 A | 4/1999 | Yeung |
| 5,690,676 A | 11/1997 | DiPoto et al. | | 5,897,564 A | 4/1999 | Schulze et al. |
| 5,690,678 A | 11/1997 | Johnson | | 5,897,574 A | 4/1999 | Bonutti |
| 5,695,497 A | 12/1997 | Stahelin et al. | | 5,899,902 A | 5/1999 | Brown et al. |
| 5,697,929 A | 12/1997 | Mellinger | | 5,899,938 A | 5/1999 | Sklar et al. |
| 5,699,657 A | 12/1997 | Paulson | | 5,908,421 A | 6/1999 | Beger et al. |

| Patent | Date | Inventor | | Patent | Date | Inventor |
|---|---|---|---|---|---|---|
| 5,908,436 A | 6/1999 | Cuschieri et al. | | 6,099,568 A | 8/2000 | Simonian et al. |
| 5,910,148 A | 6/1999 | Reimels et al. | | 6,106,545 A | 8/2000 | Egan |
| 5,911,721 A | 6/1999 | Nicholson et al. | | 6,110,128 A | 8/2000 | Andelin et al. |
| 5,918,604 A | 7/1999 | Whelan | | 6,117,160 A | 9/2000 | Bonutti |
| 5,921,986 A | 7/1999 | Bonutti | | 6,117,162 A | 9/2000 | Schmieding et al. |
| 5,925,008 A | 7/1999 | Douglas | | 6,123,710 A | 9/2000 | Pinczewski et al. |
| 5,928,267 A | 7/1999 | Bonutti et al. | | 6,132,433 A | 10/2000 | Whelan |
| 5,931,838 A | 8/1999 | Vito | | 6,132,437 A | 10/2000 | Omurtag et al. |
| 5,931,844 A | 8/1999 | Thompson et al. | | 6,139,565 A | 10/2000 | Stone et al. |
| 5,931,869 A | 8/1999 | Boucher et al. | | RE36,974 E | 11/2000 | Bonutti |
| 5,935,119 A * | 8/1999 | Guy et al. ............ 604/500 | | 6,143,017 A | 11/2000 | Thal |
| 5,935,149 A | 8/1999 | Ek | | 6,146,406 A | 11/2000 | Shluzas et al. |
| 5,938,668 A | 8/1999 | Scirica et al. | | 6,146,408 A | 11/2000 | Bartlett |
| 5,941,439 A | 8/1999 | Kammerer et al. | | 6,149,653 A | 11/2000 | Deslauriers |
| 5,941,900 A | 8/1999 | Bonutti | | 6,149,669 A | 11/2000 | Li |
| 5,944,739 A | 8/1999 | Zlock et al. | | 6,152,928 A | 11/2000 | Wenstrom, Jr. |
| 5,946,783 A | 9/1999 | Plociennik et al. | | 6,152,934 A | 11/2000 | Harper et al. |
| 5,947,915 A | 9/1999 | Thibodo, Jr. | | 6,152,936 A | 11/2000 | Christy et al. |
| 5,947,982 A | 9/1999 | Duran | | 6,152,949 A | 11/2000 | Bonutti |
| 5,948,002 A | 9/1999 | Bonutti | | 6,156,039 A | 12/2000 | Thal |
| 5,951,559 A | 9/1999 | Burkhart | | 6,156,056 A | 12/2000 | Kearns et al. |
| 5,951,560 A | 9/1999 | Simon et al. | | 6,159,234 A | 12/2000 | Bonutti et al. |
| 5,954,747 A | 9/1999 | Clark | | 6,165,203 A | 12/2000 | Krebs |
| 5,957,953 A | 9/1999 | DiPoto et al. | | 6,168,598 B1 | 1/2001 | Martello |
| 5,961,521 A | 10/1999 | Roger et al. | | 6,168,628 B1 | 1/2001 | Huebner |
| 5,961,524 A | 10/1999 | Crombie | | 6,179,840 B1 | 1/2001 | Bowman |
| 5,964,764 A | 10/1999 | West, Jr. et al. | | 6,183,461 B1 | 2/2001 | Matsuura et al. |
| 5,964,767 A | 10/1999 | Tapia et al. | | 6,187,025 B1 | 2/2001 | Machek |
| 5,964,783 A | 10/1999 | Grafton et al. | | 6,190,401 B1 | 2/2001 | Green et al. |
| 5,968,045 A | 10/1999 | Frazier | | 6,190,411 B1 | 2/2001 | Lo et al. |
| 5,968,047 A | 10/1999 | Reed | | 6,193,754 B1 | 2/2001 | Seedhom et al. |
| 5,970,697 A | 10/1999 | Jacobs et al. | | 6,200,329 B1 | 3/2001 | Fung et al. |
| 5,976,125 A | 11/1999 | Graham | | 6,200,330 B1 | 3/2001 | Benderev et al. |
| 5,976,127 A | 11/1999 | Lax | | 6,203,556 B1 * | 3/2001 | Evans et al. ............ 606/185 |
| 5,980,524 A | 11/1999 | Justin et al. | | 6,203,565 B1 | 3/2001 | Bonutti et al. |
| 5,980,539 A | 11/1999 | Kontos | | 6,203,572 B1 | 3/2001 | Johnson et al. |
| 5,980,558 A | 11/1999 | Wiley | | 6,206,883 B1 | 3/2001 | Tunc |
| 5,980,559 A * | 11/1999 | Bonutti ............ 606/232 | | 6,210,376 B1 * | 4/2001 | Grayson ............ 604/264 |
| 5,989,252 A | 11/1999 | Fumex et al. | | 6,214,012 B1 | 4/2001 | Karpman et al. |
| 5,989,256 A | 11/1999 | Kuslich et al. | | 6,221,107 B1 | 4/2001 | Steiner et al. |
| 5,989,282 A | 11/1999 | Bonutti | | 6,228,096 B1 | 5/2001 | Marchand |
| 5,993,452 A | 11/1999 | Vandewalle | | 6,231,592 B1 | 5/2001 | Bonutti et al. |
| 5,997,542 A | 12/1999 | Burke | | 6,235,057 B1 | 5/2001 | Roger et al. |
| 5,997,552 A | 12/1999 | Person et al. | | 6,238,395 B1 | 5/2001 | Bonutti |
| 6,001,100 A | 12/1999 | Sherman et al. | | 6,241,734 B1 | 6/2001 | Scribner et al. |
| 6,007,567 A | 12/1999 | Bonutti | | 6,241,747 B1 | 6/2001 | Ruff |
| 6,010,525 A | 1/2000 | Bonutti et al. | | 6,241,771 B1 | 6/2001 | Gresser et al. |
| 6,016,727 A | 1/2000 | Morgan | | 6,245,081 B1 | 6/2001 | Bowman et al. |
| 6,022,352 A | 2/2000 | Vandewalle | | 6,258,091 B1 | 7/2001 | Sevrain et al. |
| 6,022,373 A | 2/2000 | Li | | 6,267,766 B1 | 7/2001 | Burkhart |
| 6,024,758 A | 2/2000 | Thal | | 6,269,716 B1 | 8/2001 | Amis |
| 6,027,523 A | 2/2000 | Schmieding | | 6,270,518 B1 | 8/2001 | Pedlick et al. |
| 6,033,430 A | 3/2000 | Bonutti | | 6,273,890 B1 | 8/2001 | Frazier |
| 6,039,753 A | 3/2000 | Meislin | | 6,283,973 B1 | 9/2001 | Hubbard et al. |
| 6,041,485 A | 3/2000 | Pedlick et al. | | 6,283,996 B1 | 9/2001 | Chervitz et al. |
| 6,042,601 A | 3/2000 | Smith | | 6,287,325 B1 | 9/2001 | Bonutti |
| 6,045,551 A | 4/2000 | Bonutti | | 6,293,961 B2 | 9/2001 | Schwartz et al. |
| 6,045,571 A | 4/2000 | Hill et al. | | 6,296,659 B1 | 10/2001 | Foerster |
| 6,045,573 A | 4/2000 | Wenstrom, Jr. et al. | | 6,299,615 B1 | 10/2001 | Huebner |
| 6,045,574 A | 4/2000 | Thal | | 6,302,888 B1 | 10/2001 | Mellinger et al. |
| 6,047,826 A | 4/2000 | Kalinski et al. | | 6,306,156 B1 | 10/2001 | Clark |
| 6,048,343 A | 4/2000 | Mathis et al. | | 6,306,159 B1 | 10/2001 | Schwartz et al. |
| 6,051,006 A | 4/2000 | Shluzas et al. | | 6,309,405 B1 | 10/2001 | Bonutti |
| 6,053,916 A | 4/2000 | Moore | | 6,312,448 B1 | 11/2001 | Bonutti |
| 6,056,752 A | 5/2000 | Roger et al. | | 6,319,271 B1 | 11/2001 | Schwartz et al. |
| 6,056,772 A | 5/2000 | Bonutti | | 6,328,758 B1 | 12/2001 | Tornier et al. |
| 6,056,773 A | 5/2000 | Bonutti | | 6,342,060 B1 | 1/2002 | Adams |
| 6,059,817 A | 5/2000 | Bonutti et al. | | 6,343,531 B2 | 2/2002 | Amis |
| 6,062,344 A | 5/2000 | Okabe et al. | | 6,364,897 B1 | 4/2002 | Bonutti |
| 6,068,648 A | 5/2000 | Cole et al. | | 6,368,322 B1 | 4/2002 | Luks et al. |
| 6,071,305 A * | 6/2000 | Brown et al. ............ 623/1.43 | | 6,368,326 B1 | 4/2002 | Dakin et al. |
| 6,074,403 A | 6/2000 | Nord | | 6,368,343 B1 | 4/2002 | Bonutti et al. |
| 6,077,277 A | 6/2000 | Mollenauer et al. | | 6,371,124 B1 | 4/2002 | Whelan |
| 6,077,292 A | 6/2000 | Bonutti | | 6,379,361 B1 | 4/2002 | Beck, Jr. et al. |
| 6,086,591 A | 7/2000 | Bojarski | | 6,383,190 B1 | 5/2002 | Preissman |
| 6,086,592 A | 7/2000 | Rosenberg et al. | | 6,383,199 B2 | 5/2002 | Carter et al. |
| 6,086,608 A | 7/2000 | Ek et al. | | 6,387,113 B1 | 5/2002 | Hawkins et al. |
| 6,096,060 A | 8/2000 | Fitts et al. | | 6,387,129 B2 | 5/2002 | Rieser et al. |
| 6,099,530 A | 8/2000 | Simonian et al. | | 6,398,785 B2 | 6/2002 | Carchidi et al. |

| Patent | Date | Inventor |
|---|---|---|
| 6,406,479 B1 | 6/2002 | Justin et al. |
| 6,409,743 B1 | 6/2002 | Fenton, Jr. |
| 6,413,260 B1 | 7/2002 | Berrevoets et al. |
| 6,423,088 B1 | 7/2002 | Fenton, Jr. |
| 6,428,562 B2 | 8/2002 | Bonutti |
| 6,432,123 B2 | 8/2002 | Schwartz et al. |
| 6,436,124 B1 | 8/2002 | Anderson et al. |
| 6,440,134 B1 | 8/2002 | Zaccherotti et al. |
| 6,440,136 B1 | 8/2002 | Gambale et al. |
| 6,447,516 B1 | 9/2002 | Bonutti |
| 6,451,030 B2 | 9/2002 | Li et al. |
| 6,454,768 B1 | 9/2002 | Jackson |
| 6,458,134 B1 | 10/2002 | Songer et al. |
| 6,461,373 B2 | 10/2002 | Wyman et al. |
| 6,464,713 B2 | 10/2002 | Bonutti |
| 6,468,293 B2 | 10/2002 | Bonutti et al. |
| 6,471,707 B1 | 10/2002 | Miller et al. |
| 6,475,230 B1 | 11/2002 | Bonutti et al. |
| 6,482,210 B1 | 11/2002 | Skiba et al. |
| 6,485,504 B1 | 11/2002 | Johnson et al. |
| 6,497,901 B1 | 12/2002 | Royer |
| 6,500,184 B1 | 12/2002 | Chan et al. |
| 6,500,195 B2 | 12/2002 | Bonutti |
| RE37,963 E | 1/2003 | Thal |
| 6,503,267 B2 | 1/2003 | Bonutti et al. |
| 6,508,820 B2 | 1/2003 | Bales |
| 6,508,821 B1 | 1/2003 | Schwartz et al. |
| 6,508,830 B2 | 1/2003 | Steiner |
| 6,511,498 B1 | 1/2003 | Fumex et al. |
| 6,511,499 B2 | 1/2003 | Schmieding et al. |
| 6,517,542 B1 | 2/2003 | Papay et al. |
| 6,517,552 B1 | 2/2003 | Nord et al. |
| 6,517,578 B2 | 2/2003 | Hein et al. |
| 6,517,579 B1 | 2/2003 | Paulos et al. |
| 6,520,964 B2 | 2/2003 | Tallarida et al. |
| 6,520,980 B1 | 2/2003 | Foerster |
| 6,524,317 B1 | 2/2003 | Ritchart et al. |
| 6,527,777 B2 | 3/2003 | Justin |
| 6,527,794 B1 | 3/2003 | McDevitt et al. |
| 6,527,795 B1 | 3/2003 | Lizardi |
| 6,533,795 B1 | 3/2003 | Tran et al. |
| 6,533,802 B2 | 3/2003 | Bojarski et al. |
| 6,537,319 B2 | 3/2003 | Whelan |
| 6,540,750 B2 | 4/2003 | Burkhart |
| 6,540,770 B1 | 4/2003 | Tornier et al. |
| 6,544,281 B2 | 4/2003 | ElAttrache et al. |
| 6,547,564 B1 | 4/2003 | Hansson et al. |
| 6,547,778 B1 | 4/2003 | Sklar et al. |
| 6,547,800 B2 | 4/2003 | Foerster et al. |
| 6,551,330 B1 | 4/2003 | Bain et al. |
| 6,551,343 B1 | 4/2003 | Tormala et al. |
| 6,551,353 B1 * | 4/2003 | Baker et al. .................. 623/1.42 |
| 6,553,802 B2 | 4/2003 | Jacob et al. |
| 6,554,830 B1 | 4/2003 | Chappius |
| 6,554,852 B1 | 4/2003 | Oberlander |
| 6,554,862 B2 | 4/2003 | Hays et al. |
| 6,562,071 B2 | 5/2003 | Jarvinen et al. |
| 6,565,572 B2 | 5/2003 | Chappius |
| 6,565,573 B1 | 5/2003 | Ferrante et al. |
| 6,569,186 B1 | 5/2003 | Winters et al. |
| 6,569,187 B1 | 5/2003 | Bonutti et al. |
| 6,572,635 B1 | 6/2003 | Bonutti |
| 6,575,925 B1 | 6/2003 | Noble |
| 6,579,295 B1 | 6/2003 | Supinski |
| 6,582,453 B1 | 6/2003 | Tran et al. |
| 6,585,730 B1 | 7/2003 | Foerster |
| 6,585,740 B2 | 7/2003 | Schlapfer et al. |
| 6,585,750 B2 | 7/2003 | Bonutti et al. |
| 6,589,245 B1 | 7/2003 | Weiler et al. |
| 6,589,246 B1 | 7/2003 | Hack et al. |
| 6,592,609 B1 | 7/2003 | Bonutti |
| 6,595,911 B2 | 7/2003 | LoVuolo |
| 6,599,289 B1 | 7/2003 | Bojarski et al. |
| 6,599,319 B2 | 7/2003 | Knudsen et al. |
| 6,605,096 B1 | 8/2003 | Ritchart |
| 6,607,548 B2 | 8/2003 | Pohjonen et al. |
| 6,610,079 B1 | 8/2003 | Li et al. |
| 6,613,018 B2 | 9/2003 | Bagga et al. |
| 6,616,694 B1 | 9/2003 | Hart |
| 6,620,166 B1 | 9/2003 | Wenstrom, Jr. et al. |
| 6,620,185 B1 | 9/2003 | Harvie et al. |
| 6,620,195 B2 | 9/2003 | Goble et al. |
| 6,620,329 B2 | 9/2003 | Rosen et al. |
| 6,620,349 B1 | 9/2003 | Lopez |
| 6,623,492 B1 | 9/2003 | Berube et al. |
| 6,623,524 B2 | 9/2003 | Schmieding |
| 6,626,910 B1 | 9/2003 | Hugues et al. |
| 6,626,919 B1 | 9/2003 | Swanstrom |
| 6,629,977 B1 | 10/2003 | Wolf |
| 6,635,073 B2 | 10/2003 | Bonutti |
| 6,638,279 B2 | 10/2003 | Bonutti |
| 6,641,596 B1 | 11/2003 | Lizardi |
| 6,641,597 B2 | 11/2003 | Burkhart et al. |
| 6,645,227 B2 | 11/2003 | Fallin et al. |
| 6,648,921 B2 | 11/2003 | Anderson et al. |
| 6,652,562 B2 | 11/2003 | Collier et al. |
| 6,652,563 B2 | 11/2003 | Dreyfuss |
| 6,656,182 B1 | 12/2003 | Hayhurst |
| 6,656,183 B2 | 12/2003 | Colleran et al. |
| 6,658,182 B1 | 12/2003 | Gonthier et al. |
| 6,660,008 B1 | 12/2003 | Foerster et al. |
| 6,660,022 B1 | 12/2003 | Li et al. |
| 6,663,634 B2 | 12/2003 | Ahrens et al. |
| 6,663,656 B2 | 12/2003 | Schmieding et al. |
| 6,666,868 B2 | 12/2003 | Fallin |
| 6,682,549 B2 | 1/2004 | Bartlett |
| 6,685,728 B2 | 2/2004 | Sinnott et al. |
| 6,689,137 B2 | 2/2004 | Reed |
| 6,689,153 B1 | 2/2004 | Skiba |
| 6,689,154 B2 | 2/2004 | Bartlett |
| 6,692,499 B2 | 2/2004 | Tormala et al. |
| 6,712,849 B2 | 3/2004 | Re et al. |
| 6,716,224 B1 | 4/2004 | Singhatat |
| 6,716,957 B2 | 4/2004 | Tunc |
| 6,730,092 B2 | 5/2004 | Songer |
| 6,730,124 B2 | 5/2004 | Steiner |
| 6,736,799 B1 | 5/2004 | Erbe et al. |
| 6,746,483 B1 | 6/2004 | Bojarski et al. |
| 6,755,836 B1 | 6/2004 | Lewis |
| 6,761,739 B2 | 7/2004 | Shepard |
| 6,767,037 B2 | 7/2004 | Wenstrom, Jr. |
| 6,770,076 B2 | 8/2004 | Foerster |
| 6,770,084 B1 | 8/2004 | Bain et al. |
| 6,773,450 B2 | 8/2004 | Leung et al. |
| 6,780,190 B2 | 8/2004 | Maroney |
| 6,780,198 B1 | 8/2004 | Gregoire et al. |
| 6,802,862 B1 | 10/2004 | Roger et al. |
| 6,808,502 B2 | 10/2004 | Nguyen et al. |
| 6,808,526 B1 | 10/2004 | Magerl et al. |
| 6,814,741 B2 | 11/2004 | Bowman et al. |
| 6,830,572 B2 | 12/2004 | McDevitt et al. |
| 6,833,005 B1 | 12/2004 | Mantas et al. |
| 6,840,953 B2 | 1/2005 | Martinek |
| 6,860,885 B2 | 3/2005 | Bonutti |
| 6,860,895 B1 | 3/2005 | Akerfeldt et al. |
| 6,863,671 B1 | 3/2005 | Strobel et al. |
| 6,872,040 B2 | 3/2005 | Deeg et al. |
| 6,875,216 B2 | 4/2005 | Wolf |
| 6,884,249 B2 | 4/2005 | May et al. |
| 6,887,259 B2 | 5/2005 | Lizardi |
| 6,890,354 B2 | 5/2005 | Steiner et al. |
| 6,893,448 B2 | 5/2005 | O'Quinn et al. |
| 6,896,686 B2 | 5/2005 | Weber |
| 6,899,722 B2 | 5/2005 | Bonutti |
| 6,902,573 B2 | 6/2005 | Strobel et al. |
| 6,908,466 B1 | 6/2005 | Bonutti et al. |
| 6,916,292 B2 | 7/2005 | Morawski et al. |
| 6,916,321 B2 | 7/2005 | TenHuisen et al. |
| 6,921,402 B2 | 7/2005 | Contiliano et al. |
| 6,923,823 B1 | 8/2005 | Bartlett et al. |
| 6,923,824 B2 | 8/2005 | Morgan et al. |
| 6,951,565 B2 | 10/2005 | Keane et al. |
| 6,966,887 B1 | 11/2005 | Chin |
| 6,972,027 B2 | 12/2005 | Fallin et al. |
| 6,980,903 B2 | 12/2005 | Daniels et al. |
| 6,986,781 B2 | 1/2006 | Smith |
| 6,989,034 B2 | 1/2006 | Hammer et al. |
| 7,048,754 B2 | 5/2006 | Martin et al. |

| Patent/Pub No. | Date | Inventor(s) |
|---|---|---|
| 7,066,942 B2 | 6/2006 | Treace |
| 7,066,944 B2 | 6/2006 | Laufer et al. |
| 7,105,010 B2 | 9/2006 | Hart et al. |
| 7,112,221 B2 | 9/2006 | Harris et al. |
| 7,118,583 B2 | 10/2006 | O'Quinn et al. |
| 7,125,421 B2 | 10/2006 | Tremulis et al. |
| 7,137,996 B2 | 11/2006 | Steiner et al. |
| 7,141,066 B2 | 11/2006 | Steiner et al. |
| 7,144,414 B2 | 12/2006 | Harvie et al. |
| 7,153,307 B2 | 12/2006 | Scribner et al. |
| 7,153,312 B1 | 12/2006 | Torrie et al. |
| 7,153,327 B1 | 12/2006 | Metzger |
| 7,201,722 B2 | 4/2007 | Krueger |
| 7,255,675 B2 | 8/2007 | Gertner et al. |
| 7,261,716 B2 | 8/2007 | Strobel et al. |
| 7,264,634 B2 | 9/2007 | Schmieding |
| 7,285,124 B2 | 10/2007 | Foerster |
| 7,303,577 B1 | 12/2007 | Dean |
| 7,306,417 B2 | 12/2007 | Dorstewitz |
| 7,326,222 B2 | 2/2008 | Dreyfuss et al. |
| 7,390,329 B2 | 6/2008 | Westra et al. |
| 7,390,332 B2 | 6/2008 | Selvitelli et al. |
| 7,442,210 B2 | 10/2008 | Segal et al. |
| 7,585,311 B2 | 9/2009 | Green et al. |
| 7,601,165 B2 | 10/2009 | Stone |
| 7,608,098 B1 | 10/2009 | Stone et al. |
| 7,615,076 B2 | 11/2009 | Cauthen, III et al. |
| 7,632,287 B2 | 12/2009 | Baker et al. |
| 7,651,509 B2 | 1/2010 | Bojarski et al. |
| 7,658,751 B2 | 2/2010 | Stone et al. |
| 7,670,279 B2 | 3/2010 | Gertner |
| 7,678,123 B2 | 3/2010 | Chanduszko |
| 7,695,493 B2 | 4/2010 | Saadat et al. |
| 7,731,732 B2 | 6/2010 | Ken |
| 7,736,379 B2 | 6/2010 | Ewers et al. |
| 7,758,594 B2 | 7/2010 | Lamson et al. |
| 7,758,611 B2 | 7/2010 | Kato |
| 7,776,041 B1 | 8/2010 | Walters |
| 7,819,895 B2 | 10/2010 | Ginn et al. |
| 7,828,850 B2 | 11/2010 | Cauthen, III et al. |
| 7,875,058 B2 | 1/2011 | Holmes, Jr. |
| 7,981,140 B2 | 7/2011 | Burkhart |
| 8,062,334 B2 | 11/2011 | Green et al. |
| 8,075,574 B2 | 12/2011 | May et al. |
| 8,118,835 B2 | 2/2012 | Weisel et al. |
| 8,252,022 B2 | 8/2012 | Holman et al. |
| 2001/0014825 A1 | 8/2001 | Burke et al. |
| 2001/0037131 A1 | 11/2001 | Schmieding et al. |
| 2001/0037153 A1 | 11/2001 | Rockwood et al. |
| 2001/0041916 A1 | 11/2001 | Bonutti |
| 2001/0041937 A1 | 11/2001 | Rieser et al. |
| 2001/0041938 A1 | 11/2001 | Hein |
| 2001/0044639 A1 | 11/2001 | Levinson |
| 2001/0047206 A1 | 11/2001 | Sklar et al. |
| 2001/0051816 A1 | 12/2001 | Enzerink et al. |
| 2001/0053934 A1 | 12/2001 | Schmieding |
| 2002/0001964 A1 | 1/2002 | Choi |
| 2002/0004669 A1 | 1/2002 | Bartlett |
| 2002/0007182 A1 | 1/2002 | Kim |
| 2002/0010513 A1 | 1/2002 | Schmieding |
| 2002/0013608 A1 | 1/2002 | ElAttrache et al. |
| 2002/0019649 A1 | 2/2002 | Sikora et al. |
| 2002/0029066 A1 | 3/2002 | Foerster |
| 2002/0055780 A1 | 5/2002 | Sklar |
| 2002/0058966 A1 | 5/2002 | Tormala et al. |
| 2002/0099411 A1 | 7/2002 | Bartlett |
| 2002/0111653 A1 | 8/2002 | Foerster |
| 2002/0120270 A1 | 8/2002 | Trieu et al. |
| 2002/0120292 A1 | 8/2002 | Morgan |
| 2002/0123752 A1 | 9/2002 | Schultheiss et al. |
| 2002/0128684 A1 | 9/2002 | Foerster |
| 2002/0147463 A1 | 10/2002 | Martinek |
| 2002/0161401 A1 | 10/2002 | Steiner |
| 2002/0161439 A1 | 10/2002 | Strobel et al. |
| 2002/0169452 A1 | 11/2002 | Tormala et al. |
| 2002/0169477 A1* | 11/2002 | Demopulos et al. .......... 606/215 |
| 2002/0169478 A1 | 11/2002 | Schwartz et al. |
| 2002/0173788 A1 | 11/2002 | Bojarski et al. |
| 2002/0188298 A1 | 12/2002 | Chan |
| 2003/0009235 A1 | 1/2003 | Manrique et al. |
| 2003/0023268 A1 | 1/2003 | Lizardi |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1* | 2/2003 | Malaviya et al. .......... 623/14.12 |
| 2003/0036801 A1 | 2/2003 | Schwartz et al. |
| 2003/0065391 A1 | 4/2003 | Re et al. |
| 2003/0078603 A1 | 4/2003 | Schaller et al. |
| 2003/0078617 A1 | 4/2003 | Schwartz et al. |
| 2003/0083662 A1 | 5/2003 | Middleton |
| 2003/0088251 A1 | 5/2003 | Braun et al. |
| 2003/0088272 A1 | 5/2003 | Smith |
| 2003/0105477 A1 | 6/2003 | Schwartz et al. |
| 2003/0120309 A1 | 6/2003 | Colleran et al. |
| 2003/0130694 A1 | 7/2003 | Bojarski et al. |
| 2003/0135214 A1 | 7/2003 | Fetto et al. |
| 2003/0135239 A1 | 7/2003 | Gabriel et al. |
| 2003/0135963 A1 | 7/2003 | Holbrook et al. |
| 2003/0152522 A1 | 8/2003 | Miller et al. |
| 2003/0167072 A1 | 9/2003 | Oberlander |
| 2003/0167090 A1 | 9/2003 | Chervitz et al. |
| 2003/0171811 A1 | 9/2003 | Steiner et al. |
| 2003/0176865 A1 | 9/2003 | Supinski |
| 2003/0176919 A1 | 9/2003 | Schmieding |
| 2003/0181925 A1 | 9/2003 | Bain et al. |
| 2003/0195528 A1 | 10/2003 | Ritchart |
| 2003/0195564 A1 | 10/2003 | Tran et al. |
| 2003/0208210 A1 | 11/2003 | Dreyfuss et al. |
| 2003/0212456 A1 | 11/2003 | Lipchitz et al. |
| 2003/0220660 A1 | 11/2003 | Kortenbach et al. |
| 2003/0225459 A1 | 12/2003 | Hammer et al. |
| 2004/0002734 A1 | 1/2004 | Fallin et al. |
| 2004/0006345 A1 | 1/2004 | Vlahos et al. |
| 2004/0006346 A1 | 1/2004 | Holmen et al. |
| 2004/0015171 A1 | 1/2004 | Bojarski et al. |
| 2004/0015172 A1 | 1/2004 | Biedermann et al. |
| 2004/0024456 A1 | 2/2004 | Brown et al. |
| 2004/0044391 A1 | 3/2004 | Porter |
| 2004/0087981 A1 | 5/2004 | Berube et al. |
| 2004/0092936 A1 | 5/2004 | Miller et al. |
| 2004/0098051 A1 | 5/2004 | Fallin et al. |
| 2004/0098053 A1 | 5/2004 | Tran |
| 2004/0111117 A1 | 6/2004 | Colleran et al. |
| 2004/0122431 A1 | 6/2004 | Biedermann et al. |
| 2004/0133211 A1 | 7/2004 | Raskin et al. |
| 2004/0138664 A1 | 7/2004 | Bowman |
| 2004/0138683 A1* | 7/2004 | Shelton et al. .............. 606/151 |
| 2004/0138704 A1 | 7/2004 | Gambale et al. |
| 2004/0138706 A1 | 7/2004 | Abrams et al. |
| 2004/0143344 A1 | 7/2004 | Malaviya et al. |
| 2004/0147932 A1 | 7/2004 | Burkinshaw et al. |
| 2004/0153103 A1 | 8/2004 | Schwartz et al. |
| 2004/0153153 A1 | 8/2004 | Elson et al. |
| 2004/0162579 A1 | 8/2004 | Foerster |
| 2004/0166169 A1 | 8/2004 | Malaviya et al. |
| 2004/0182968 A1 | 9/2004 | Gentry |
| 2004/0187314 A1 | 9/2004 | Johnson |
| 2004/0204722 A1 | 10/2004 | Sikora et al. |
| 2004/0220574 A1* | 11/2004 | Pelo et al. ...................... 606/73 |
| 2004/0225292 A1 | 11/2004 | Sasso et al. |
| 2004/0225305 A1 | 11/2004 | Ewers et al. |
| 2004/0236353 A1 | 11/2004 | Bain et al. |
| 2004/0236373 A1 | 11/2004 | Anspach |
| 2004/0243139 A1 | 12/2004 | Lewis et al. |
| 2004/0243178 A1 | 12/2004 | Haut et al. |
| 2004/0249394 A1 | 12/2004 | Morris et al. |
| 2004/0267164 A1 | 12/2004 | Rhodes et al. |
| 2004/0267265 A1 | 12/2004 | Kyle |
| 2004/0267270 A1 | 12/2004 | Jacobs et al. |
| 2004/0267276 A1 | 12/2004 | Camino et al. |
| 2004/0267277 A1 | 12/2004 | Zannis et al. |
| 2004/0267304 A1 | 12/2004 | Zannis et al. |
| 2005/0027307 A1 | 2/2005 | Schwartz et al. |
| 2005/0033363 A1* | 2/2005 | Bojarski et al. .............. 606/228 |
| 2005/0038426 A1 | 2/2005 | Chan |
| 2005/0055027 A1 | 3/2005 | Yeung et al. |
| 2005/0064042 A1 | 3/2005 | Vunjak-Novakovic et al. |
| 2005/0074495 A1 | 4/2005 | Schwartz et al. |

| | | |
|---|---|---|
| 2005/0090828 A1 | 4/2005 | Alford |
| 2005/0096696 A1 | 5/2005 | Forsberg |
| 2005/0096697 A1 | 5/2005 | Forsberg et al. |
| 2005/0107828 A1 | 5/2005 | Reese |
| 2005/0119531 A1 | 6/2005 | Sharratt |
| 2005/0125031 A1 | 6/2005 | Pipenhagen et al. |
| 2005/0125073 A1 | 6/2005 | Orban et al. |
| 2005/0137600 A1 | 6/2005 | Jacobs et al. |
| 2005/0137624 A1 | 6/2005 | Fallman |
| 2005/0149033 A1 | 7/2005 | McGuire et al. |
| 2005/0159812 A1 | 7/2005 | Dinger et al. |
| 2005/0165416 A1 | 7/2005 | Bojarski et al. |
| 2005/0165482 A1 | 7/2005 | Goldhahn et al. |
| 2005/0187565 A1 | 8/2005 | Baker et al. |
| 2005/0187577 A1 | 8/2005 | Selvitelli et al. |
| 2005/0203620 A1 | 9/2005 | Steiner et al. |
| 2005/0222618 A1 | 10/2005 | Dreyfuss et al. |
| 2005/0222619 A1 | 10/2005 | Dreyfuss et al. |
| 2005/0228448 A1 | 10/2005 | Li |
| 2005/0251159 A1 | 11/2005 | Ewers et al. |
| 2005/0251208 A1 | 11/2005 | Elmer et al. |
| 2005/0267479 A1 | 12/2005 | Morgan et al. |
| 2005/0267533 A1 | 12/2005 | Gertner |
| 2005/0277961 A1 | 12/2005 | Stone et al. |
| 2005/0283040 A1 | 12/2005 | Greenhalgh |
| 2005/0283156 A1 | 12/2005 | Schmieding et al. |
| 2005/0283158 A1 | 12/2005 | West |
| 2005/0283192 A1 | 12/2005 | Torrie et al. |
| 2006/0004410 A1 | 1/2006 | Nobis et al. |
| 2006/0030884 A1 | 2/2006 | Yeung et al. |
| 2006/0030948 A1 | 2/2006 | Manrique et al. |
| 2006/0036265 A1 | 2/2006 | Dant |
| 2006/0064126 A1 | 3/2006 | Fallin et al. |
| 2006/0069334 A1 | 3/2006 | Moskowitz |
| 2006/0084943 A1 | 4/2006 | Rosenman et al. |
| 2006/0100627 A1* | 5/2006 | Stone et al. .............. 606/72 |
| 2006/0116685 A1 | 6/2006 | Urbanski et al. |
| 2006/0121084 A1 | 6/2006 | Borden et al. |
| 2006/0135958 A1 | 6/2006 | Marissen et al. |
| 2006/0149266 A1 | 7/2006 | Cordasco |
| 2006/0167481 A1 | 7/2006 | Baker et al. |
| 2006/0167482 A1 | 7/2006 | Swain et al. |
| 2006/0173492 A1 | 8/2006 | Akerfeldt et al. |
| 2006/0178680 A1 | 8/2006 | Nelson et al. |
| 2006/0189993 A1 | 8/2006 | Stone |
| 2006/0190042 A1 | 8/2006 | Stone et al. |
| 2006/0212055 A1 | 9/2006 | Karabey et al. |
| 2006/0229671 A1 | 10/2006 | Steiner et al. |
| 2006/0235407 A1 | 10/2006 | Wang et al. |
| 2006/0247642 A1* | 11/2006 | Stone et al. .............. 606/73 |
| 2006/0253130 A1 | 11/2006 | Wolniewicz |
| 2006/0271192 A1 | 11/2006 | Olsen et al. |
| 2006/0280768 A1* | 12/2006 | Hwang et al. ............ 424/423 |
| 2006/0282082 A1 | 12/2006 | Fanton et al. |
| 2006/0282085 A1 | 12/2006 | Stone et al. |
| 2006/0293709 A1 | 12/2006 | Bojarski et al. |
| 2007/0005080 A1 | 1/2007 | Wolniewicz et al. |
| 2007/0010857 A1 | 1/2007 | Sugimoto et al. |
| 2007/0016305 A1 | 1/2007 | Chudik |
| 2007/0032800 A1 | 2/2007 | Ortiz et al. |
| 2007/0055255 A1 | 3/2007 | Siegel |
| 2007/0060922 A1 | 3/2007 | Dreyfuss |
| 2007/0067025 A1 | 3/2007 | Schwartz |
| 2007/0073307 A1 | 3/2007 | Scribner et al. |
| 2007/0078435 A1 | 4/2007 | Stone et al. |
| 2007/0083236 A1 | 4/2007 | Sikora et al. |
| 2007/0093847 A1 | 4/2007 | Scribner et al. |
| 2007/0142838 A1 | 6/2007 | Jordan |
| 2007/0185532 A1 | 8/2007 | Stone et al. |
| 2007/0185568 A1* | 8/2007 | Schwartz .............. 623/1.42 |
| 2007/0191849 A1 | 8/2007 | ElAttrache et al. |
| 2007/0219558 A1 | 9/2007 | Deutsch |
| 2007/0239209 A1 | 10/2007 | Fallman |
| 2007/0239275 A1 | 10/2007 | Willobee |
| 2007/0250163 A1 | 10/2007 | Cassani |
| 2008/0027446 A1 | 1/2008 | Stone et al. |
| 2008/0046009 A1 | 2/2008 | Albertorio et al. |
| 2008/0065114 A1 | 3/2008 | Stone et al. |
| 2008/0082127 A1 | 4/2008 | Stone et al. |
| 2008/0082128 A1 | 4/2008 | Stone |
| 2008/0132753 A1 | 6/2008 | Goddard |
| 2008/0132932 A1 | 6/2008 | Hoeppner et al. |
| 2008/0140092 A1 | 6/2008 | Stone et al. |
| 2008/0140093 A1 | 6/2008 | Stone et al. |
| 2008/0161852 A1 | 7/2008 | Kaiser et al. |
| 2008/0188936 A1 | 8/2008 | Ball et al. |
| 2008/0221527 A1 | 9/2008 | Bradley et al. |
| 2008/0255613 A1 | 10/2008 | Kaiser et al. |
| 2008/0262544 A1 | 10/2008 | Burkhart |
| 2008/0268064 A1 | 10/2008 | Woodell-May |
| 2008/0269674 A1 | 10/2008 | Stone |
| 2008/0275477 A1 | 11/2008 | Sterrett et al. |
| 2008/0312689 A1 | 12/2008 | Denham et al. |
| 2009/0018655 A1 | 1/2009 | Brunelle et al. |
| 2009/0054928 A1 | 2/2009 | Denham et al. |
| 2009/0062854 A1 | 3/2009 | Kaiser et al. |
| 2009/0082805 A1 | 3/2009 | Kaiser et al. |
| 2009/0138002 A1 | 5/2009 | Fenton |
| 2009/0156997 A1 | 6/2009 | Trenhaile |
| 2009/0177233 A1 | 7/2009 | Malek |
| 2009/0204146 A1 | 8/2009 | Kaiser et al. |
| 2009/0240335 A1 | 9/2009 | Arcenio et al. |
| 2009/0306711 A1 | 12/2009 | Stone et al. |
| 2009/0312776 A1 | 12/2009 | Kaiser et al. |
| 2009/0318960 A1 | 12/2009 | Burkhart |
| 2009/0318961 A1 | 12/2009 | Stone et al. |
| 2010/0042114 A1 | 2/2010 | Schaffhausen |
| 2010/0087857 A1 | 4/2010 | Stone et al. |
| 2010/0145384 A1 | 6/2010 | Stone et al. |
| 2010/0191342 A1 | 7/2010 | Byrd et al. |
| 2010/0211075 A1 | 8/2010 | Stone |
| 2010/0256677 A1 | 10/2010 | Albertorio et al. |
| 2010/0268273 A1 | 10/2010 | Albertorio et al. |
| 2010/0268275 A1 | 10/2010 | Stone et al. |
| 2010/0270306 A1 | 10/2010 | Shiffer |
| 2010/0292792 A1 | 11/2010 | Stone et al. |
| 2010/0305698 A1 | 12/2010 | Metzger et al. |
| 2010/0305709 A1 | 12/2010 | Metzger et al. |
| 2010/0312341 A1 | 12/2010 | Kaiser et al. |
| 2011/0009885 A1 | 1/2011 | Graf et al. |
| 2011/0087284 A1 | 4/2011 | Stone et al. |
| 2011/0098727 A1 | 4/2011 | Kaiser et al. |
| 2011/0106153 A1 | 5/2011 | Stone et al. |
| 2011/0160767 A1 | 6/2011 | Stone et al. |
| 2011/0160768 A1 | 6/2011 | Stone et al. |
| 2011/0208239 A1 | 8/2011 | Stone et al. |
| 2011/0208240 A1 | 8/2011 | Stone et al. |
| 2011/0213416 A1 | 9/2011 | Kaiser |
| 2011/0218625 A1 | 9/2011 | Berelsman et al. |
| 2011/0270278 A1 | 11/2011 | Overes et al. |
| 2012/0197271 A1 | 8/2012 | Astorino et al. |

FOREIGN PATENT DOCUMENTS

| | | |
|---|---|---|
| AU | 440266 | 10/1967 |
| AU | 2223767 | 11/1968 |
| AU | 5028569 | 8/1970 |
| AU | 5850469 | 1/1971 |
| AU | 5963869 | 2/1971 |
| AU | 1505470 | 11/1971 |
| AU | 3615171 | 5/1973 |
| AU | 7110887 | 10/1987 |
| AU | 639410 | 11/1989 |
| AU | 651929 | 8/1994 |
| DE | 2529669 | 3/1976 |
| DE | 2747312 | 4/1979 |
| DE | 2818254 | 10/1979 |
| DE | 2919009 | 11/1979 |
| DE | 3027138 | 12/1981 |
| DE | 3225620 | 2/1983 |
| DE | 3136083 | 3/1983 |
| DE | 233303 | 2/1986 |
| DE | 4127550 | 2/1993 |
| DE | 4302397 | 7/1993 |
| DE | 29621340 | 5/1998 |
| DE | 19841252 | 3/2000 |
| EP | 0108912 | 5/1984 |
| EP | 0129442 | 12/1984 |
| EP | 0172130 | 2/1986 |

| | | |
|---|---|---|
| EP | 0241240 | 10/1987 |
| EP | 0241792 | 10/1987 |
| EP | 0260970 | 3/1988 |
| EP | 0270704 | 6/1988 |
| EP | 0282789 | 9/1988 |
| EP | 0315371 | 5/1989 |
| EP | 0317406 | 5/1989 |
| EP | 0340159 | 11/1989 |
| EP | 0346183 | 12/1989 |
| EP | 0349173 | 1/1990 |
| EP | 0374088 | 6/1990 |
| EP | 0409364 | 1/1991 |
| EP | 0415915 | 3/1991 |
| EP | 0440991 | 8/1991 |
| EP | 0441065 | 8/1991 |
| EP | 0451932 | 10/1991 |
| EP | 0464480 | 1/1992 |
| EP | 0497079 | 8/1992 |
| EP | 0502509 | 9/1992 |
| EP | 0502698 | 9/1992 |
| EP | 520177 | 12/1992 |
| EP | 0546726 | 6/1993 |
| EP | 0574707 | 12/1993 |
| EP | 0582514 | 2/1994 |
| EP | 0591991 | 4/1994 |
| EP | 0598219 | 5/1994 |
| EP | 0611551 A1 | 8/1994 |
| EP | 0627203 | 12/1994 |
| EP | 0651979 | 5/1995 |
| EP | 0669110 | 8/1995 |
| EP | 0686373 | 12/1995 |
| EP | 0702933 | 3/1996 |
| EP | 0775473 | 5/1997 |
| EP | 0913123 | 5/1999 |
| EP | 0913131 | 5/1999 |
| EP | 99121106 | 10/1999 |
| EP | 991210527 | 10/1999 |
| EP | 0995409 | 4/2000 |
| EP | 1013229 | 6/2000 |
| EP | 1093773 | 4/2001 |
| EP | 1093774 | 4/2001 |
| EP | 1555945 | 7/2005 |
| FR | 2622790 | 5/1989 |
| FR | 2655840 | 6/1991 |
| FR | 2682867 | 4/1993 |
| FR | 2687911 | 9/1993 |
| FR | 2688689 | 9/1993 |
| FR | 2704140 | 10/1994 |
| FR | 2717070 | 9/1995 |
| FR | 2723528 | 2/1996 |
| FR | 2744010 | 8/1997 |
| FR | 2745999 | 9/1997 |
| FR | 2770764 | 5/1999 |
| GB | 401677 | 11/1933 |
| GB | 1413477 | 11/1975 |
| GB | 1485681 | 9/1977 |
| GB | 2083751 | 3/1982 |
| GB | 2118474 | 11/1983 |
| GB | 2227175 | 7/1990 |
| GB | 2253147 | 9/1992 |
| GB | 2312376 | 10/1997 |
| GB | 2403416 A | 1/2005 |
| JP | 5362911 | 5/1978 |
| JP | 5362912 | 5/1978 |
| JP | 5374942 | 6/1978 |
| JP | 5378230 | 6/1978 |
| JP | 62159647 | 7/1987 |
| JP | 62295657 | 12/1987 |
| JP | 5269160 | 10/1993 |
| JP | 5300917 | 11/1993 |
| JP | 751292 | 2/1995 |
| JP | 10211213 | 8/1998 |
| WO | WO-8300615 | 3/1983 |
| WO | WO-8603666 | 7/1986 |
| WO | WO-8701270 | 3/1987 |
| WO | WO-8901767 | 3/1989 |
| WO | WO-8909030 | 10/1989 |
| WO | WO-8910096 | 11/1989 |
| WO | WO-9008510 | 8/1990 |
| WO | WO-9203980 | 3/1992 |
| WO | WO-9314705 | 8/1993 |
| WO | WO-9315694 | 8/1993 |
| WO | WO-9502373 | 1/1995 |
| WO | WO-9503003 | 2/1995 |
| WO | WO-9529637 | 11/1995 |
| WO | WO-9532670 | 12/1995 |
| WO | WO-9629029 | 9/1996 |
| WO | WO-9737603 | 10/1997 |
| WO | WO-9812991 | 4/1998 |
| WO | WO-9812992 | 4/1998 |
| WO | WO-9822047 | 5/1998 |
| WO | WO-9822048 | 5/1998 |
| WO | WO-9901084 | 1/1999 |
| WO | WO-9912480 | 3/1999 |
| WO | WO-9944544 | 9/1999 |
| WO | WO-0040159 | 7/2000 |
| WO | WO-0139671 | 6/2001 |
| WO | WO-0236020 | 5/2002 |
| WO | WO-03005914 A1 | 1/2003 |
| WO | WO-03071962 | 9/2003 |
| WO | WO-03077772 | 9/2003 |
| WO | WO-2005104992 | 11/2005 |
| WO | WO-2008002550 A2 | 1/2008 |

OTHER PUBLICATIONS

"Make your next tendon repair an open-and-shut case. The Teno Fix® Tendon Repair System", Teno Fix® brochure, 2003 (2 pages) Ortheon® Medical.
US 6,238,418, 05/2001, Schwartz et al. (withdrawn).
Invitation to Pay Additional Fees mailed Jun. 9, 2011 for PCT/US2001/026349 claiming benefit of U.S. Appl. No. 12/938,902, filed Nov. 3, 2010; and U.S. Appl. No. 12/719,337, filed Mar. 8, 2010.
U.S. Appl. No. 11/408,282, filed Apr. 20, 2006.
U.S. Appl. No. 11/347,661, filed Feb. 3, 2006.
U.S. Appl. No. 11/294,694, filed Dec. 5, 2005.
U.S. Appl. No. 10/984,624, filed Nov. 9, 2004.
U.S. Appl. No. 10/784,031, filed Feb. 20, 2004, Schaffhausen.
U.S. Appl. No. 10/983,236, filed Nov. 5, 2004, Stone et al.
U.S. Appl. No. 11/347,661, filed Feb. 3, 2006, Stone et al.
U.S. Appl. No. 11/347,662, filed Feb. 3, 2006, Stone et al.
U.S. Appl. No. 11/386,071, filed Mar. 21, 2006, Stone et al.
U.S. Appl. No. 11/504,882, filed Aug. 16, 2006, Stone et al.
U.S. Appl. No. 11/541,505, filed Sep. 29, 2006, Stone et al.
U.S. Appl. No. 11/541,506, filed Sep. 29, 2006, Stone et al.
U.S. Appl. No. 11/784,821, filed Apr. 10, 2007, Kaiser et al.
U.S. Appl. No. 11/869,440, filed Oct. 9, 2007, Stone et al.
U.S. Appl. No. 11/935,681, filed Nov. 6, 2007, Stone et al.
U.S. Appl. No. 12/014,340, filed Jan. 15, 2008, Stone et al.
U.S. Appl. No. 12/014,399, filed Jan. 15, 2008, Stone et al.
U.S. Appl. No. 12/029,861, filed Feb. 12, 2008, Hoeppner et al.
U.S. Appl. No. 12/196,405, filed Aug. 22, 2008, Kaiser et al.
U.S. Appl. No. 12/196,407, filed Aug. 22, 2008, Denham et al.
U.S. Appl. No. 12/196,410, filed Aug. 22, 2008, Denham et al.
U.S. Appl. No. 12/196,398, filed Aug. 22, 2008, Kaiser et al.
U.S. Appl. No. 12/474,802, filed May 29, 2009, Kaiser et al.
U.S. Appl. No. 12/489,168, filed Jun. 22, 2009, Stone et al.
U.S. Appl. No. 12/489,181, filed Jun. 22, 2009, Stone et al.
U.S. Appl. No. 12/606,752, filed Oct. 27, 2009, Schaffhausen.
U.S. Appl. No. 12/570,854, filed Sep. 30, 2009, Stone et al.
U.S. Appl. No. 12/702,067, filed Feb. 8, 2010, Stone et al.
U.S. Appl. No. 12/719,337, filed Mar. 8, 2010, Stone et al.
U.S. Appl. No. 12/788,966, filed May 27, 2010, Metzger et al.
U.S. Appl. No. 12/788,973, filed May 27, 2010, Metzger et al.
U.S. Appl. No. 12/788,978, filed May 27, 2010, Stone et al.
U.S. Appl. No. 12/828,977, filed Jul. 1, 2010, Stone et al.
U.S. Appl. No. 12/915,962, filed Oct. 29, 2010, Kaiser et al.
U.S. Appl. No. 12/938,902, filed Nov. 3, 2010, Stone et al.
U.S. Appl. No. 12/976,328, filed Dec. 22, 2010, Stone et al.
U.S. Appl. No. 13/045,689, filed Mar. 11, 2011, Stone et al.
U.S. Appl. No. 13/045,691, filed Mar. 11, 2011, Stone et al.
U.S. Appl. No. 13/098,927, filed May 2, 2011, Stone et al.
U.S. Appl. No. 13/098,897, filed May 2, 2011, Stone et al.
U.S. Appl. No. 13/102,182, filed May 6, 2011, Kaiser.

U.S. Appl. No. 13/109,672, filed May 17, 2011, Berelsman.
U.S. Appl. No. 13/111,564, filed May 19, 2011, Stone.
U.S. Appl. No. 13/177,153, filed Jul. 6, 2011, Stone.
U.S. Appl. No. 13/181,729, filed Jul. 26, 2011, Denham et al.
U.S. Appl. No. 13/269,097, filed Oct. 7, 2011, Stone et al.
U.S. Appl. No. 13/278,341, filed Oct. 21, 2011, Kaiser et al.
U.S. Appl. No. 13/281,009, filed Oct. 25, 2011, Stone et al.
U.S. Appl. No. 13/281,016, filed Oct. 25, 2011, Kaiser et al.
U.S. Appl. No. 13/293,825, filed Nov. 10, 2011, Norton et al.
U.S. Appl. No. 13/295,126, filed Nov. 14, 2011, Denham et al.
"AperFix® System Surgical Technique Guide. Single Tunnel Double Bundle.™" Cayenne Medical brochure. (Aug. 2008) 8 sheets.
"Bio-Intrafix Tibial Soft Tissue Fasteners, Building on the Legacy of IntraFix," brochure. DePuy Mitek,(Feb. 2007) 6 sheets.
"Biomechanical Evaluation of the Biomet Sports Medicine JurggerKnot™ Soft Anchor in Porcine Bone," Study completed Jan. 2010. Biomet Sports Medicine Research and Development, Warsaw, Indiana. 2 pages.
"JuggerKnot™ Soft Anchor Midfoot Repair," brochure. Biomet Sports Medicine (Jul. 2011) 12 sheets.
"JuggerKnot™ Soft Anchor. It's Small. It's strong. And it's all suture . . . " Ordering Information brochure. Biomet Sports Medicine (Jun. 2011) 2 sheets.
"JuggerKnot™ Soft Anchor. Labral Repair," brochure. Biomet Sports Medicine (Apr. 2011) 12 sheets.
International Search Report and Written Opinion mailed Jul. 28, 2011 for PCT/US2011/026349 claiming benefit of U.S. Appl. No. 12/938,902, filed Nov. 3, 2010; and U.S. Appl. No. 12/719,337, filed Mar. 8, 2010.
International Search Report and Written Opinion mailed Oct. 14, 2011 for PCT/US2011/038188 filed May 26, 2011 claiming benefit of U.S. Appl. No. 12/788,973, filed May 27, 2010 and U.S. Appl. No. 12/788,966, filed May 27, 2010.
Invitation to Pay Additional Fees mailed Aug. 5, 2011 for PCT/US2011/038188 claiming benefit of U.S. Appl. No. 12/788,973, filed May 27, 2010 and U.S. Appl. No. 12/788,966, filed May 27, 2010.
"EZ Loc Femoral Fixation Device," copyright 2005 Arthrotek, Inc. (8 sheets).
"PANALOK Anchor with PDS II and ETHIBOND Suture", Mitek Products ETHICON, 1997.
"SE Graft Tensioning System Surgical Technique," Linvatec Corporation copyright 2003, 2004.

"Technique for ACL Reconstruction with Acufex Director Drill Guide and Endobutton CL," by Thomas D. Roseberg, copyright 1999 Smith & Nephew.
A. Weiler, et al; Biodegradierbare Interferenzschrauben in der Kreuzbandchirurgie; OP-Journal 14 pp. 278-284; 1998.
Arthrotek, A Biomet Company; Knees; Sure fire Hybrid Meniscal Device, Fall 2004.
Arthrotek, A Biomet Company; Sure fire Hybrid Meniscal Device; Launch Date: Fall AANA 2004.
Bio-Intrafix (TCP/PLA & Intrafix, Tibial Soft Tissue Fasteners, by DePuy Mitek, 6 sheets, (date unknown).
F. Alan Barber, M.D., "Uses and Abuses of Sutures and Anchors," Shoulder Scope, San Diego Shoulder Arthroscopy Library, May 2000.
F. Alan Barber, M.D., "Using Sutures and Anchors," San Diego Shoulder Arthroscopy Course, 17th Annual Meeting, Dec. 2006.
Flavia Namie Azato, et al. "Traction endurance biomechanical study of metallic suture anchors at different insertion angles," Acta ortop. bras., vol. 11, No. 1, Sao Paulo, Jan./Mar. 2003.
Hecker AT, et al., "Pull-out strength of suture anchors for rotator cuff and Bankart lesion repairs," Am J Sports Med. 1993.
Lawhorn, M.D., Keith, MaxFire™ Meniscal Repair Device with Zip Loop™ Technology, Biomet Sports Medicine, Feb. 29, 2008.
Mark D. Miller et al.; "Pitfalls Associated with FasT-Fix Meniscal Repair," Arthroscopy: The Journal of Arthroscopic and Related Surgery, vol. 18, No. 8 Oct. 2002: pp. 939-943.
Opus Medical; The AutoCuff System; www.opusmedical.com; 2003.
Patrick Hunt, et al.; Development of a Perforated Biodegradable Interference Screw; Arthroscopy: The Journal of Arthroscopic and Related Surgery, vol. 21, No. 3; pp. 258-265; Mar. 2005.
Roy Alan Majors, M.D.; "Meniscal repairs: proven techniques and current trends," Lippincott Williams & Wilkins, Inc.; 2002.
Shoulder Arthroscopy; pp. H-2-H-22, Dec. 2002.
Smith & Nephew Endoscopy, "Endoscopic Meniscal Repair Using the T-Fix;" 1996.
Smith & Nephew, "Fast-Fix," Meniscal Repair System; 2001.
Stuart E. Fromm, M.D., RapidLoc, Meniscal Repair System, Mitek Products, Ethicon, 2001.
ToggleLoc™ Femoral Fixation Device, Arthrotek, Mar. 31, 2006.
Invitation to Pay Additional Fees mailed Jul. 19, 2012, for PCT/US2012/037703 claiming benefit of U.S. Appl. No. 13/109,667, filed May 7, 2011.

* cited by examiner

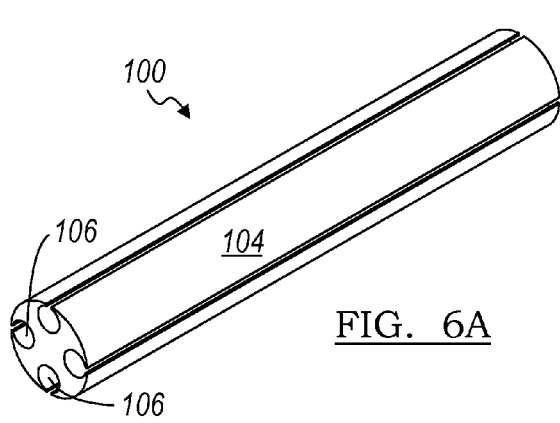
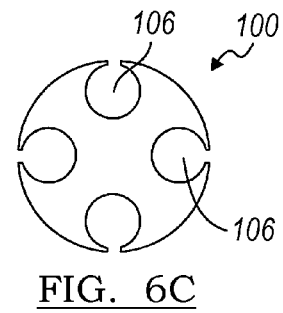
FIG. 6A
FIG. 6C
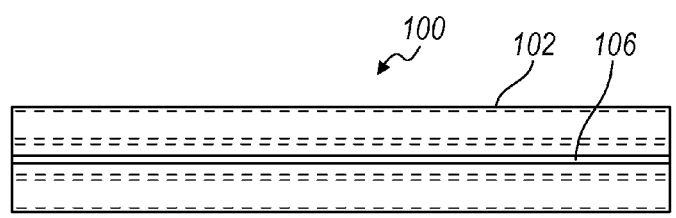
FIG. 6B
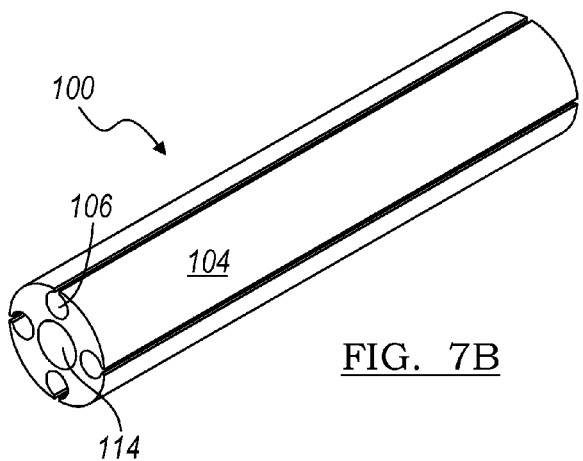
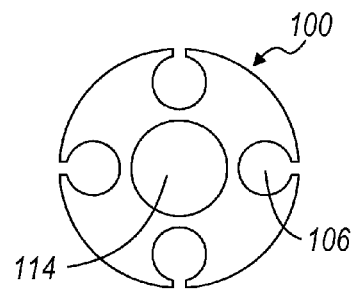
FIG. 7B
FIG. 7C
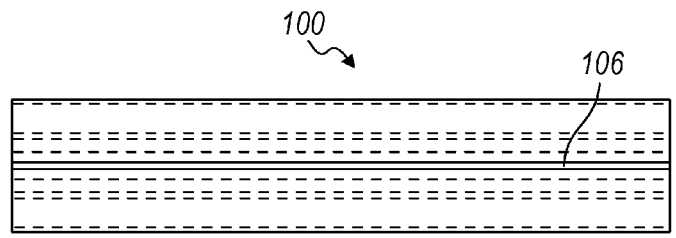
FIG. 7A

SOFT TISSUE CONDUIT DEVICE AND METHOD

CROSS-REFERENCE TO RELATED APPLICATIONS

This application is a divisional of U.S. patent application Ser. No. 11/408,282 filed on Apr. 20, 2006 now abandoned, which is a continuation-in-part of U.S. patent application Ser. No. 11/347,661 filed on Feb. 3, 2006, and issued as U.S. Pat. No. 7,749,250, and also a continuation-in-part of U.S. patent application Ser. No. 11/294,694 filed Dec. 5, 2005, and issued as U.S. Pat. No. 7,914,539, which is a continuation-in-part of U.S. patent application Ser. No. 10/984,624 filed Nov. 9, 2004, and issued as U.S. Pat. No. 7,608,098. The disclosures of the above applications are incorporated herein by reference.

INTRODUCTION

Tears caused by trauma or disease in soft tissue, such as cartilage, ligament, or muscle, can be repaired by suturing and/or use of various fixation devices. Various tissue fixation devices have been developed for facilitating suturing and are effective for their intended purposes.

Although the existing soft tissue fixation devices can be satisfactory for their intended purposes, there is still a need for new devices that provide conduits for facilitating healing and promoting soft tissue vascularity.

SUMMARY

The present teachings provide a soft tissue conduit device. The device includes an elongated body having an outer surface, the elongated body defining a plurality of longitudinal external channels, each longitudinal channel defining a conduit open to the outer surface of the elongated body, each conduit operable to conduct a biological material in soft tissue.

The present teachings also provide a method of conducting biological materials in soft tissue. The method includes inserting an elongated conduit device into the soft tissue and through a defect in the soft tissue, and conducting biological materials along at least one longitudinal channel defined on an outer surface of the conduit device into the soft tissue. The conduit device is externally threaded.

In another aspect, the method includes inserting an externally threaded elongated body in meniscal tissue. The elongated body has a plurality of external longitudinal channels. Each longitudinal channel is open to an outer surface of the elongated body and has a keyhole-shaped cross-section with a substantially circular portion and a narrow opening to the outer surface of the elongated body. Each longitudinal channel extends between a first area of the meniscal tissue having a first vascularity and a second area of the meniscal tissue having a second vascularity different from the first vascularity. The method also includes delivering biological materials from the first area to the second area through at the circular portion of the least one longitudinal channel.

In yet another aspect, the method includes passing a suture strand through a longitudinal bore of a conduit device, the conduit device having an externally threaded elongated body, the elongated body having a plurality of external longitudinal channels, coupling the suture strand to a fixation device, the fixation device inserted through a meniscal defect, and returning the suture strand through the longitudinal bore of the conduit device to form a suture loop. The method also includes inserting the conduit device through the meniscal defect such that each longitudinal channel extends between a first area having a first vascularity and a second area having a second vascularity different from the first vascularity, delivering biological materials from the first area to the second area through the longitudinal channels, and securing the suture loop with a knot.

Further areas of applicability of the present invention will become apparent from the description provided hereinafter. It should be understood that the description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 6A is an isometric view of a conduit device according to the present teachings;

FIG. 6B is a side view of the conduit device of FIG. 6A;

FIG. 6C is an end view of the conduit device of FIG. 6A;

FIG. 7A is an isometric view of a conduit device according to the present teachings;

FIG. 7B is a side view of the conduit device of FIG. 7A;

FIG. 7C is an end view of the conduit device of FIG. 7A;

DESCRIPTION OF VARIOUS ASPECTS

The following description is merely exemplary in nature and is in no way intended to limit the invention, its application, or uses. For example, although the present teachings are illustrated for repairing meniscal defects in knee surgery, the present teachings can be used to repair and facilitate healing or regeneration of any injured soft tissue.

Figure 1A:
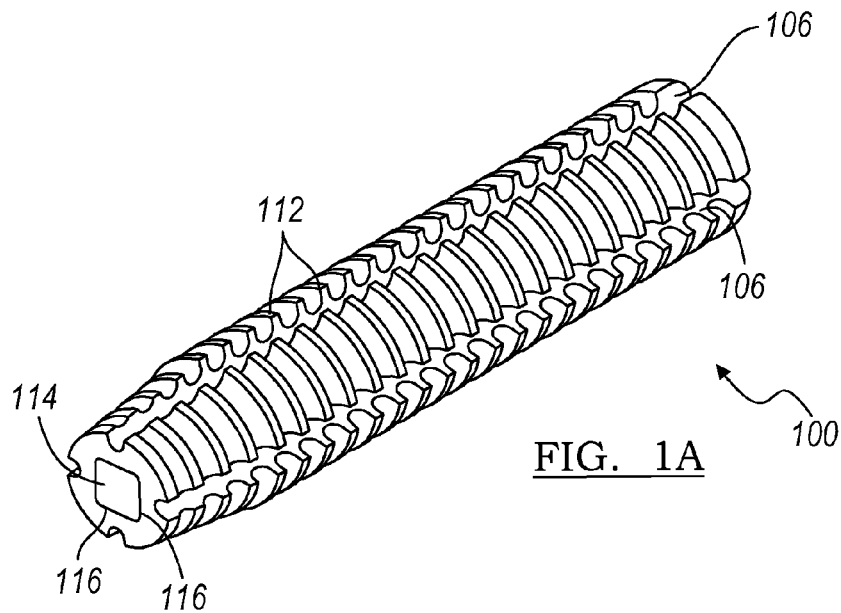
FIG. 1A is an isometric view of a conduit device according to the present teachings.
Figure 1B:
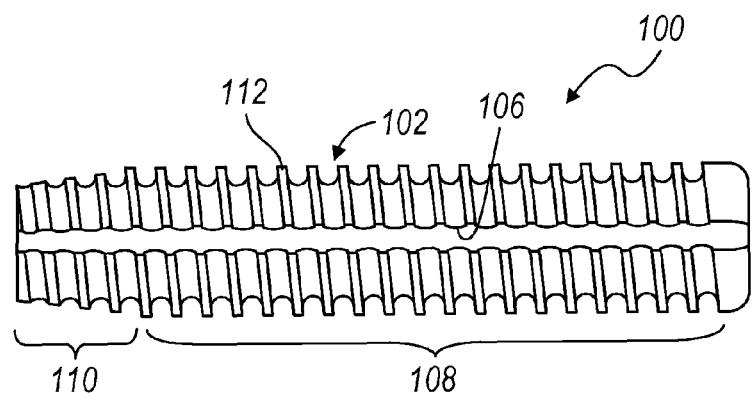
FIG. 1B is a side view of the conduit device of FIG. 1A.
Figure 1C:
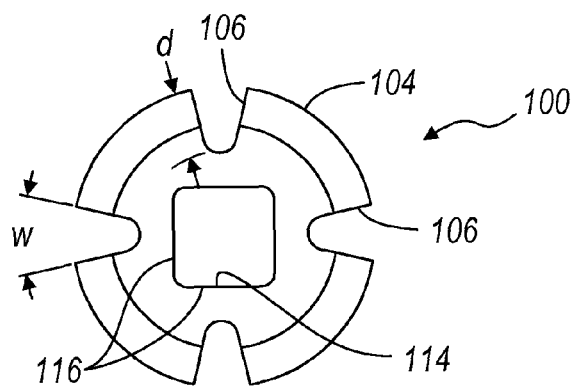
FIG. 1C is an end view of the conduit device of FIG. 1A.
Figure 1D:
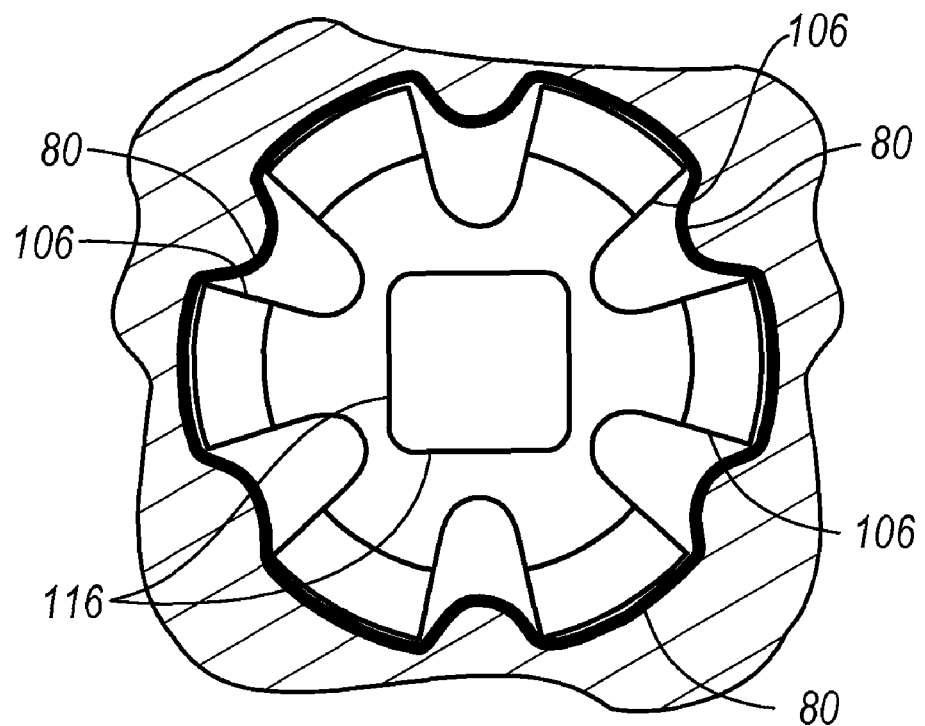
FIG. 1D is an end view of a conduit device illustrating adequate tenting of soft tissue according to the present teachings.
Figure 1E:
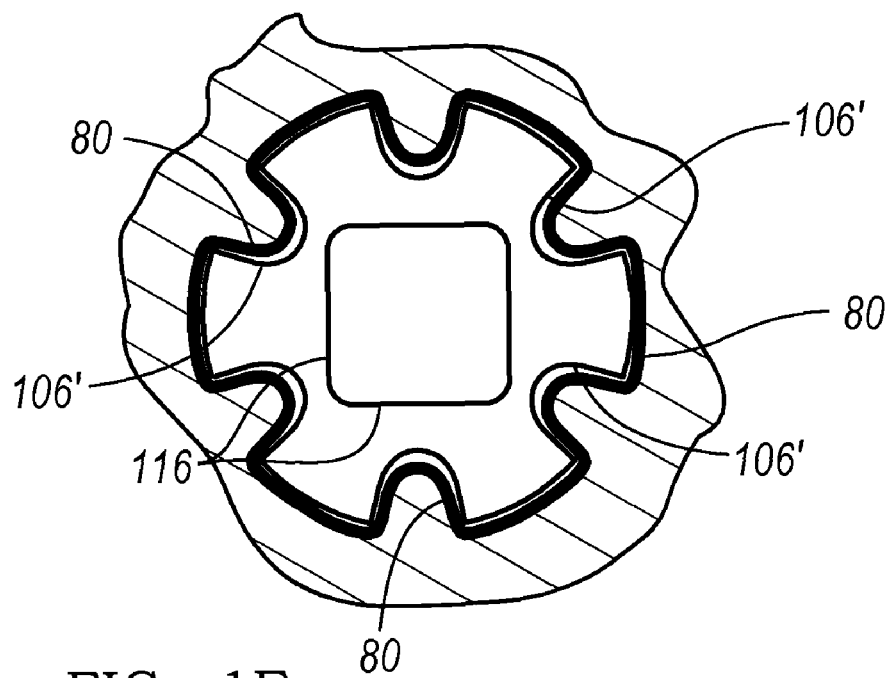
FIG. 1E is an end view of a conduit device illustrating inadequate tenting of soft tissue.

Referring to FIGS. 1A-C, an exemplary soft tissue conduit device 100 according to the present teachings includes an elongated body 102 having an outer surface 104 and a plurality of longitudinal external channels 106 extending along the entire length of the body 102. The channels 106 are shaped such that when the conduit device 100 is inserted into soft tissue, the channels 106 can serve as conduits for conducting biological materials, such as nutrients, into the tissue from outside the tissue or between first and second areas of the tissue, such as, for example, between healthy tissue and injured or torn tissue, or between areas of different vascularity, such as between red-red (vascular), red-white (semi-vascular) and white (avascular) tissue areas of a meniscus. The channels 106 can provide a vascularity path in the tissue for facilitating healing or repair. As such, each channel 106 can have a width "w" and a depth "d" that allows the tissue to envelope or form a "tent" over the channel 106 without blocking the channel 106. Referring to FIG. 1D, deep channels 106 exemplify a shape that provides satisfactory "tenting" or draping of tissue 80 over the channels 106. Referring to FIG. 1E, shallow channels 106' illustrate inadequate tenting of tissue 80 over the channels 106', with the tissue at least partially entering the channels 106'. Satisfactory tenting of tissue 80 allows unobstructed or relatively unrestricted flow of nutrients or other biological materials along the channels 106. Typical aspect ratios d/w bare less than 1, such as, for example, 0.5, 0.8, etc.

Various biological materials can be delivered through the channels 106 by external cannulas or other pumping devices during or after implantation. Such biological materials can be in the form of autologous cells derived from blood or bone marrow aspirate, for example, or other appropriate exogenous biological materials. Native or endogenous biological materials can also be carried after implantation from a vascular region of the soft tissue 80 to the injured site by inserting the conduit device 100 such that the conduit device 100 extends from a vascular region of the soft tissue to the injured site. Additionally or alternatively, biological materials in the form of platelet gels can be deposited in the channels 106 before implantation, as another mechanism of biological material delivery, including nutrient, delivery.

Referring to FIGS. 1A-1C, the body 102 of the conduit device 100 can include a cylindrical portion 108 of constant dimensions and a tapered portion 110. The body 102 can also include a plurality of blunt, rounded, and generally non-cutting ridges or threads 112 that are interrupted by the channels 106. The body 102 can be cannulated with an internal longitudinal bore 114. The longitudinal bore 114 can include a plurality of facets or sides 116 for engaging a driver or other inserter for inserting the conduit device 100 in the soft tissue 80. The bore 114 can have, for example, a square, triangular, hexagonal or other shape configured to engage the driver non-rotatably.

Figure 2A:
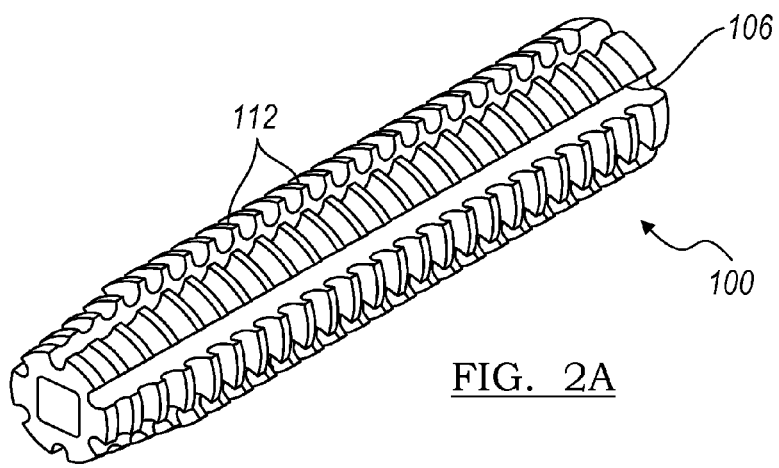
FIG. 2A is an isometric view of a conduit device according to the present teachings.
Figure 2B:
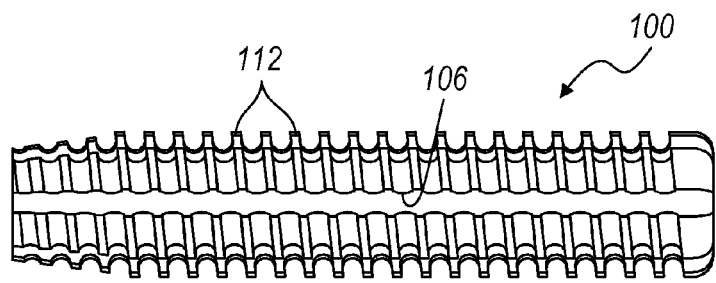
FIG. 2B is a side view of the conduit device of FIG. 2A.
Figure 2C:
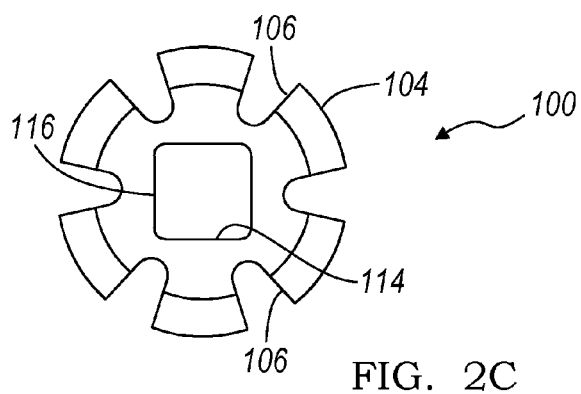
FIG. 2C is an end view of the conduit device of FIG. 2A.
Figure 3A:
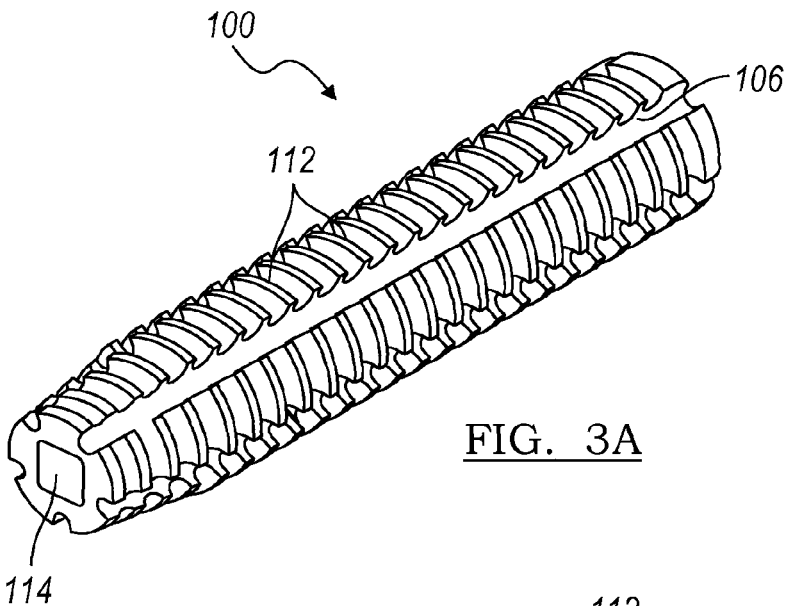
FIG. 3A is an isometric view of a conduit device according to the present teachings.
Figure 3B:
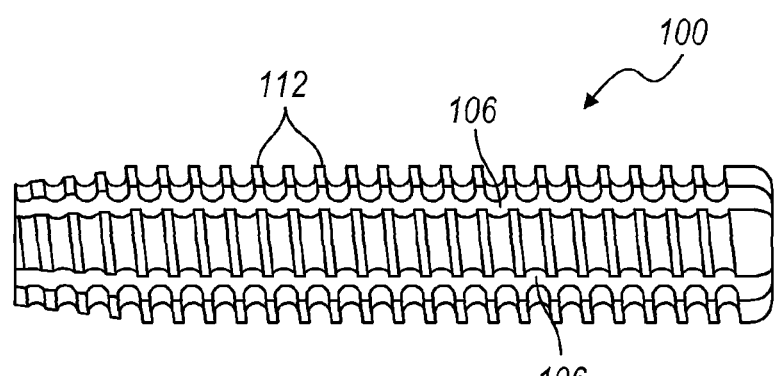
FIG. 3B is a side view of the conduit device of FIG. 3A.
Figure 3C:
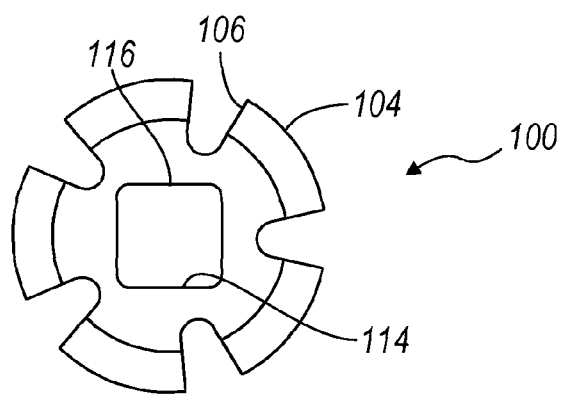
FIG. 3C is an end view of the conduit device of FIG. 3A.

Referring to FIGS. 1A-1C, 2A-2C, and 3A-3C, exemplary conduit devices 100 having channels 106 with rounded V-shaped cross-sections are illustrated. FIGS. 1A-1C illustrate an aspect of the conduit device 100 with four channels 106 arranged, for example, symmetrically relative to the four sides 116 of a square bore 114, although asymmetrical arrangements can also be used. FIGS. 2A-2C illustrate an aspect of the conduit device 100 with six channels 106 arranged symmetrically relative to the four sides 116 of the square bore 114. FIGS. 3A-3C illustrate an aspect of the conduit device 100 with five channels 106 arranged asymmetrically relative to the four sides 116 of a square bore 114.

Figure 4A:
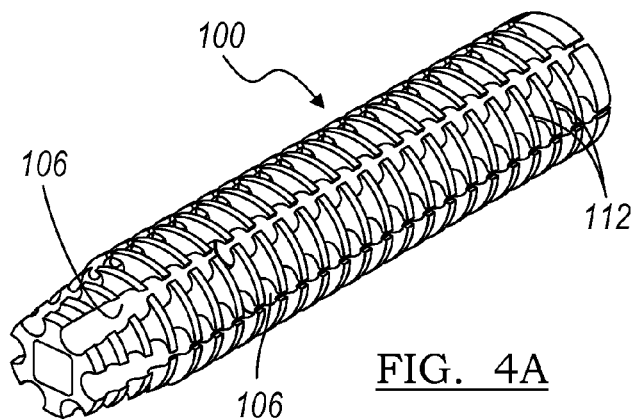
FIG. 4A is an isometric view of a conduit device according to the present teachings.
Figure 4C:
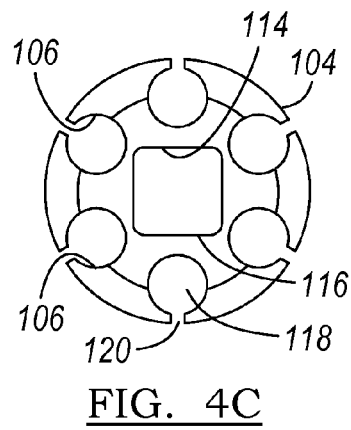
FIG. 4C is an end view of the conduit device of FIG. 4A.
Figure 4B:
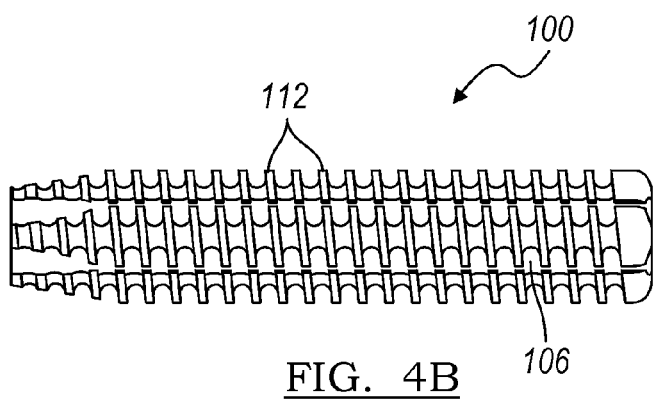
FIG. 4B is a side view of the conduit device of FIG. 4A.

Referring to FIGS. 4A-4C, an exemplary conduit device 100 having channels 106 with keyhole-shaped cross-sections is illustrated. The keyhole shape can include a substantially circular portion 118 and a narrow slot-like opening 120 to the outer surface 104 of the body 102. The keyhole shape can be used to provide a path for substantial volume of biological materials or nutrients with good tenting of tissue 80 over the channels 106. It will be appreciated, however, that a different number of channels 106 and a variety of different channel shapes can be used as conduits for the conduit device 100.

Figure 5:
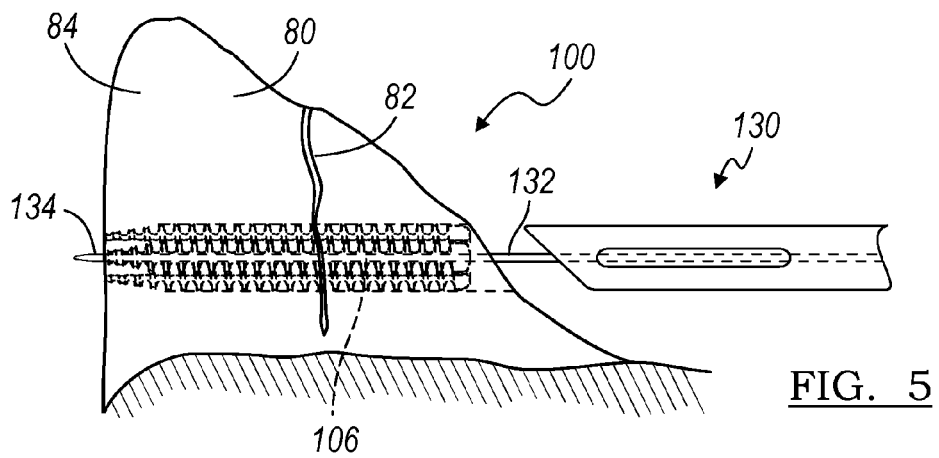
FIG. 5 illustrates a method of inserting a conduit device in soft tissue according to the present teachings.

Referring to FIG. 5, an exemplary method of using the conduit device 100 is illustrated. A driver 130 can be used to insert the conduit device 100 through a tear or other defect or injury 82 in the soft tissue or meniscus 80. The driver 130 can have a shaft 132 configured to engage the bore 114 of the body 102 of the conduit device 100 to facilitate inserting and guiding the conduit device 100 into the tissue 80. The shaft 132 of the driver 130 can also include a sharp tip 134 for facilitating the insertion of the conduit device 100 into tissue 80. The driver 130 can be used to rotate the conduit device 100 such that the blunt threads 112 push the tissue 80 aside during the insertion of the conduit device 100. The conduit device 100 can be used to connect areas of good vascularity 84 of the soft tissue 80, such as, for example, the outer surface of a meniscus, with the site of the defect 82 or other areas of low or no vascularity, and can also serve as a fixation device that can bridge the defect 82 and/or bring closer together opposite sites of torn or damaged tissue at the defect 82.

Referring to FIGS. 6A-6C and 7A-7C, the conduit device 100 can have a body 102 with a substantially cylindrical shape of constant diameter without external threads or ridges, and having an outer surface 104 interrupted by a plurality of longitudinal channels 106. The body 102 can be otherwise solid (non-cannulated) as illustrated in FIGS. 6A-6C, or cannulated with an internal longitudinal bore 114, as shown in FIGS. 7A-7C. The channels 106 can have different cross-sectional shapes, including the illustrated keyhole shapes for improved tissue tenting. The non-threaded conduit devices 100 of FIGS. 6A-6C and 7A-7C can be used with various anchors, buttons, toggles or other fixation devices 140, as illustrated in FIGS. 8A-8B and 9.

Figure 10A:
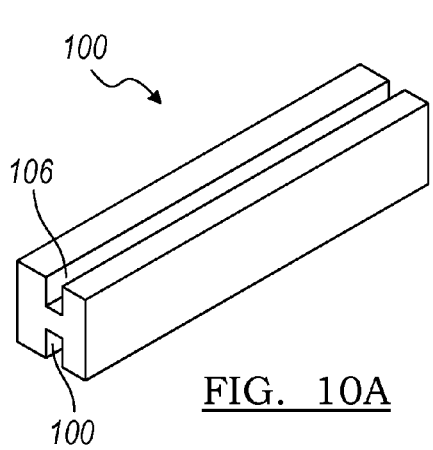
FIG. 10A is an isometric view of a conduit device according to the present teachings.
Figure 10B:
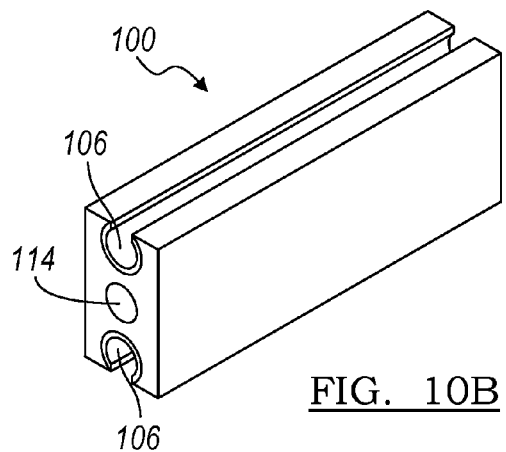
FIG. 10B is an isometric view of a conduit device according to the present teachings.

Referring to FIGS. 10A and 10B, exemplary conduit devices 100 having flat or parallelepiped bodies are illustrated. The channels 106 can be square or V-shaped or U-shaped or key-hole shaped, for example. The conduit devices 100 can include central bores 114 or can be solid. It will be appreciated that conduit devices 100 of various other shapes can be used, such as oval, square, rectangular, circular, or other shapes, and having channels 106 of different shapes. The conduit devices can be coupled with fixation devices 140 using sutures or flexible strands 142 passing through the central bore 114 or through two channels 106, as discussed below in reference to FIGS. 8A-8B.

Figure 8A:
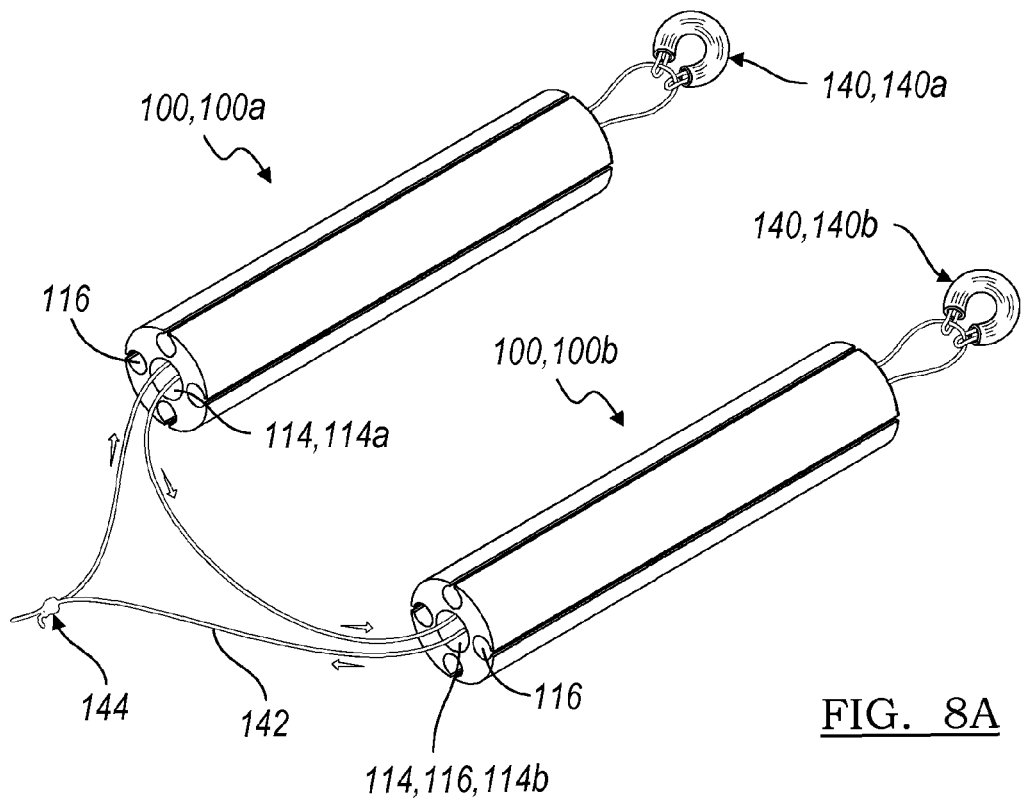
FIG. 8A illustrates a method of connecting two conduit devices with two fixation devices according to the present teachings.
Figure 9:
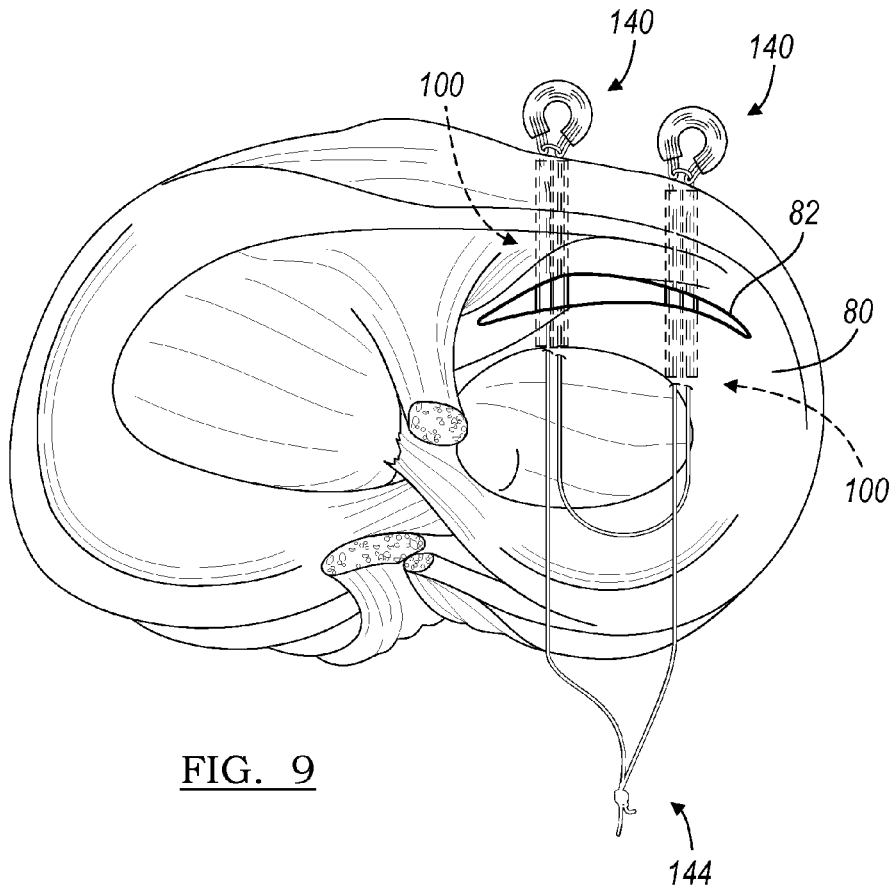
FIG. 9 illustrates a method of repairing a meniscal tear according to the present teachings.

Referring to FIG. 8A, two cannulated conduit devices 100a, 100b can be coupled with corresponding fixation devices 140a, 140b using a suture or other elongated flexible strand 142. The flexible strand 142 can define a loop that passes through the first bore 114a, connects to the corresponding fixation device 140a, returns through the same bore 114a, passes through the second bore 114b, connects to the second fixation device 140b, returns through the second bore 114b, and closes the loop with a knot, button or other retainer 144.

Figure 8B:
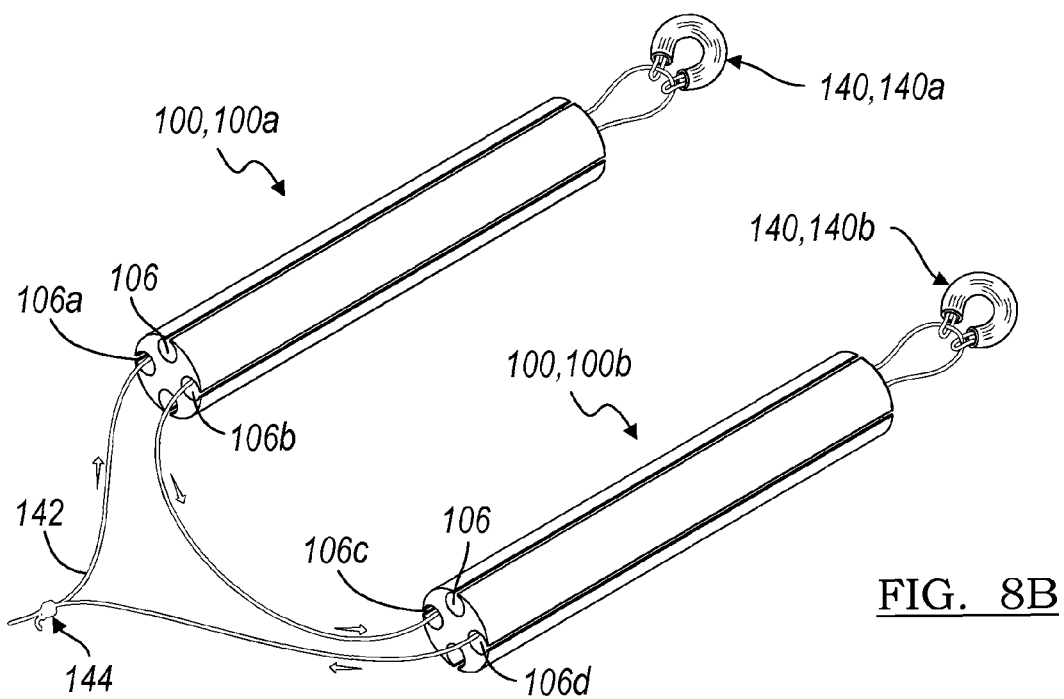
FIG. 8B illustrates a method of connecting two conduit devices with two fixation devices according to the present teachings.

Similarly, two non-cannulated conduit devices 100a, 100b can be coupled with corresponding fixation devices 140a, 140b using the flexible strand 142, as shown in FIG. 8B. The flexible strand 142 can define a loop that passes through a first external channel 106a of the first conduit device 100a, connects to the corresponding fixation device 140a and returns through a second channel 106b of the first conduit device 100a. The flexible strand 142 then passes through a third channel 106c of the second conduit device 100b, connects to the second fixation device 140b, returns through a fourth channel 106d of the second conduit device 100b, and closes the loop with a retainer 144.

Referring to FIG. 9, two conduit devices 100 are shown coupled with two fixation devices 140, which are inserted through a tear 82 in a meniscus and secured by tightening the loop defined by the flexible strand 142. The implantation of the conduit devices 100 and the fixation devices 140 for reducing or closing the tear 82 can be performed according to the methods described in co-pending parent patent application Ser. No. 11/347,661 filed Feb. 3, 2006, and incorporated herein by reference.

It will be appreciated from the above description that the conduit devices 100 can be used for many applications in which biological materials or nutrients are needed to be delivered to a soft tissue site or transferred from one tissue site to another. The longitudinal channels 106 of the devices coupled with dimensions that facilitate tenting of tissue provide unobstructed and continuous paths for the flow or delivery of such biological materials and nutrients.

The foregoing discussion discloses and describes merely exemplary arrangements of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A method of conducting biological materials in meniscal tissue, the method comprising:
   providing a conduit device having a first end and a second end and an externally threaded elongated body extending from the first end to the second end along a longitudinal axis of the conduit device, the elongated body having a plurality of external longitudinal channels, each longitudinal channel extending from the first end to the second end along the longitudinal axis, each longitudinal channel being open to an outer surface of the elongated body and having a keyhole-shaped cross-section with a substantially circular portion and a slot-like opening to the outer surface of the elongated body, each slot-like opening being narrower that a width of each circular portion;
   implanting the conduit device through the meniscal tissue such that each longitudinal channel extends between a first area of the meniscal tissue having a first vascularity and a second area of the meniscal tissue having a second vascularity different from the first vascularity; and
   delivering via an external cannula biological materials from the first area to the second area along and within the circular portion of each longitudinal channel from the first end toward the second end of the conduit device.

2. The method of claim 1, further comprising coupling the conduit device to a tissue fixation device.

3. The method of claim 2, wherein coupling the conduit device to a tissue fixation device includes forming a flexible strand loop between the conduit device and the fixation device.

4. The method of claim 3, wherein the loop passes through an internal longitudinal bore of the conduit device.

5. The method of claim 3, wherein the loop passes through one of the longitudinal channels of the conduit device.

6. The method of claim 1, further comprising tenting the meniscal tissue over the slot-like openings of the longitudinal channels without obstructing the circular portion of the longitudinal channels.

7. The method of claim 1, further comprising:
   delivering biological materials to each longitudinal channel during or after implantation.

8. The method of claim 1, further comprising:
   attaching biological materials to each longitudinal channel before implanting the conduit device.

9. A method of conducting biological materials in meniscal tissue, the method comprising:
   providing a conduit device having a first end, a second end, a longitudinal axis and a longitudinal bore between the first end the second end;
   passing a suture strand through the longitudinal bore of the conduit device, the conduit device having a plurality of external longitudinal channels not communicating with the longitudinal bore;
   coupling the suture strand with a fixation device, the fixation device inserted through a meniscal defect;
   returning the suture strand through the longitudinal bore of the conduit device to form a suture loop;
   implanting the conduit device through the meniscal defect such that each longitudinal channel extends between a first area having a first vascularity and a second area having a second vascularity different from the first vascularity;
   delivering, via an external cannula, biological materials from the first area to the second area along and within the longitudinal channels from the first end toward the second end of each longitudinal channel; and
   securing the suture loop with a knot.

10. The method of claim 9, wherein delivering biological materials from the first area to the second area through the longitudinal channels comprises delivering biological materials through a substantially circular portion of a cross-section of each of the longitudinal channels, the circular portion leading to a slot narrower than the circular portion and extending to an outer surface of the conduit device.

11. The method of claim 10, further comprising tenting the meniscal tissue over the slots of the cross-sections of the corresponding longitudinal channels without obstructing the circular portion of the longitudinal channels.

12. The method of claim 9, wherein delivering biological materials from the first area to the second area through the longitudinal channels comprises delivering biological materials through a substantially V-shaped cross-section of each of the longitudinal channels.

13. The method of claim 9, wherein implanting the conduit device through the meniscal defect comprises positioning the conduit device to span a meniscal tear.

14. The method of claim 13, further comprising
   passing the suture strand through a second fixation device and a second conduit device; and
   closing the meniscal tear.

* * * * *

UNITED STATES PATENT AND TRADEMARK OFFICE
CERTIFICATE OF CORRECTION

PATENT NO. : 8,317,825 B2
APPLICATION NO. : 12/419491
DATED : November 27, 2012
INVENTOR(S) : Kevin T. Stone It is certified that error appears in the above-identified patent and that said Letters Patent is hereby corrected as shown below:

Title Page 2, Item (56), line 6, References Cited, Other Publications,
Delete "401, 677, 11/1933, Autenrieth" and insert --401,677, 4/1889, Autenrieth--.

In the Specification
Column 1, Line 58; After "through" delete "at".
Column 3, Line 45; After "nutrient" delete ",".

In the Claims
Column 5, Line 51, Claim 1; Delete "narrower that" and insert --narrower than--.

Signed and Sealed this
Eleventh Day of November, 2014

Michelle K. Lee
*Deputy Director of the United States Patent and Trademark Office*